United States Patent
Allec et al.

(10) Patent No.: US 12,066,702 B1
(45) Date of Patent: Aug. 20, 2024

(54) SYSTEMS AND METHODS FOR DISTINGUISHING BETWEEN A USER AND AN OBJECT

(71) Applicant: Apple Inc., Cupertino, CA (US)

(72) Inventors: Nicholas Paul Joseph Allec, Menlo Park, CA (US); Maximillian Chase Bruggeman, Cincinnati, OH (US); Ueyn L Block, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 447 days.

(21) Appl. No.: 16/581,704

(22) Filed: Sep. 24, 2019

Related U.S. Application Data

(60) Provisional application No. 62/736,270, filed on Sep. 25, 2018.

(51) Int. Cl.
| | | |
|---|---|---|
| *A61B 5/00* | (2006.01) | |
| *G02B 3/08* | (2006.01) | |
| *G02B 27/09* | (2006.01) | |
| *G02F 1/133* | (2006.01) | |
| *A61B 5/024* | (2006.01) | |

(52) U.S. Cl.
CPC ........ *G02F 1/13318* (2013.01); *A61B 5/6844* (2013.01); *G02B 3/08* (2013.01); *G02B 27/0922* (2013.01); *A61B 5/02427* (2013.01)

(58) Field of Classification Search
CPC ............ G02B 27/0172; G02B 27/0101; G02B 6/12004; A61B 1/07
See application file for complete search history.

(56) References Cited

U.S. PATENT DOCUMENTS

| | | |
|---|---|---|
| 4,931,767 A | 6/1990 | Albrecht et al. |
| 5,287,376 A | 2/1994 | Paoli |
| 5,483,261 A | 1/1996 | Yasutake |
| 5,488,204 A | 1/1996 | Mead et al. |
| 5,488,678 A | 1/1996 | Taneya |
| 5,617,439 A | 4/1997 | Kakimoto |
| 5,644,667 A | 7/1997 | Tabuchi |

(Continued)

FOREIGN PATENT DOCUMENTS

| | | |
|---|---|---|
| EP | 1403985 | 3/2004 |
| EP | 1432045 | 6/2004 |

(Continued)

OTHER PUBLICATIONS

U.S. Appl. No. 16/650,804, filed Mar. 25, 2020, Arbore et al.
(Continued)

*Primary Examiner* — Deborah L Malamud
(74) *Attorney, Agent, or Firm* — Brownstein Hyatt Farber Schreck, LLP

(57) ABSTRACT

Disclosed herein is an electronic device including an optical sensing unit for distinguishing between a user's body and an object. The optical sensing unit can include a plurality of light detectors, a plurality of first light emitters, and a plurality of second light emitters. The plurality of first light emitters can measure physiological information of the user, and the plurality of second light emitters can measure a state of the device. The device can include one or more optical components, which can allow the plurality of second light emitters to emit first light towards the strap attached to the device and second light towards the edges of the device.

14 Claims, 20 Drawing Sheets

(56) References Cited

U.S. PATENT DOCUMENTS

| | | |
|---|---|---|
| 5,742,631 A | 4/1998 | Paoli |
| 5,825,352 A | 10/1998 | Bisset et al. |
| 5,835,079 A | 11/1998 | Shieh |
| 5,848,088 A | 12/1998 | Mori et al. |
| 5,880,411 A | 3/1999 | Gillespie et al. |
| 5,940,556 A | 8/1999 | Moslehi et al. |
| 6,083,172 A | 7/2000 | Baker, Jr. et al. |
| 6,094,270 A | 7/2000 | Uomori |
| 6,122,042 A | 9/2000 | Wunderman et al. |
| 6,188,391 B1 | 2/2001 | Seely et al. |
| 6,310,610 B1 | 10/2001 | Beaton et al. |
| 6,330,378 B1 | 12/2001 | Forrest |
| 6,345,133 B1 | 2/2002 | Morozov |
| 6,393,185 B1 | 5/2002 | Deacon |
| 6,526,300 B1 | 2/2003 | Kiani et al. |
| 6,533,729 B1 | 3/2003 | Khair |
| 6,584,136 B2 | 6/2003 | Ju et al. |
| 6,594,409 B2 | 7/2003 | Dutt et al. |
| 6,615,065 B1 | 9/2003 | Barrett et al. |
| 6,628,686 B1 | 9/2003 | Sargent |
| 6,657,723 B2 | 12/2003 | Cohen |
| 6,662,033 B2 | 12/2003 | Casciani et al. |
| 6,690,387 B2 | 2/2004 | Zimmerman et al. |
| 6,795,622 B2 | 9/2004 | Forrest |
| 6,892,449 B1 | 5/2005 | Brophy et al. |
| 6,940,182 B2 | 9/2005 | Hilton et al. |
| 6,947,639 B2 | 9/2005 | Singh |
| 6,952,504 B2 | 10/2005 | Bi |
| 6,987,906 B2 | 1/2006 | Nakama et al. |
| 7,015,894 B2 | 3/2006 | Morohoshi |
| 7,054,517 B2 | 5/2006 | Mossberg |
| 7,058,245 B2 | 6/2006 | Farahi |
| 7,079,715 B2 | 7/2006 | Kish |
| 7,184,064 B2 | 2/2007 | Zimmerman et al. |
| 7,203,401 B2 | 4/2007 | Mossberg |
| 7,203,426 B2 | 4/2007 | Wu et al. |
| 7,209,611 B2 | 4/2007 | Joyner |
| 7,237,858 B2 | 7/2007 | Igarashi |
| 7,245,379 B2 | 7/2007 | Schwabe |
| 7,269,356 B2 | 9/2007 | Winzer |
| 7,283,694 B2 | 10/2007 | Welch |
| 7,314,451 B2 | 1/2008 | Halperin et al. |
| 7,324,195 B2 | 1/2008 | Packirisamy et al. |
| 7,366,364 B2 | 4/2008 | Singh |
| 7,444,048 B2 | 10/2008 | Peters et al. |
| 7,447,393 B2 | 11/2008 | Yan |
| 7,460,742 B2 | 12/2008 | Joyner |
| 7,477,384 B2 | 1/2009 | Schwabe |
| 7,483,599 B2 | 1/2009 | Dominic et al. |
| 7,526,007 B2 | 4/2009 | Chua et al. |
| 7,558,301 B2 | 7/2009 | Lin et al. |
| 7,616,110 B2 | 11/2009 | Crump et al. |
| 7,643,860 B2 | 1/2010 | Gueissaz |
| 7,663,607 B2 | 2/2010 | Hotelling et al. |
| 7,680,364 B2 | 3/2010 | Nilsson |
| 7,689,075 B2 | 3/2010 | Jenkins et al. |
| 7,720,328 B2 | 5/2010 | Yan |
| 7,798,634 B2 | 9/2010 | Miyahara et al. |
| 7,885,302 B2 | 2/2011 | Eberhard |
| 7,885,492 B2 | 2/2011 | Welch |
| 7,974,504 B2 | 7/2011 | Nagarajan |
| 8,019,400 B2 | 9/2011 | Diab et al. |
| 8,175,670 B2 | 5/2012 | Baker, Jr. et al. |
| 8,300,994 B2 | 10/2012 | Welch et al. |
| 8,378,811 B2 | 2/2013 | Crump et al. |
| 8,463,345 B2 | 6/2013 | Kuhn et al. |
| 8,515,217 B2 | 8/2013 | Bernasconi et al. |
| 8,559,775 B2 | 10/2013 | Babie et al. |
| 8,564,784 B2 | 10/2013 | Wang et al. |
| 8,618,930 B2 | 12/2013 | Papadopoulos et al. |
| 8,700,111 B2 | 4/2014 | LeBoeuf et al. |
| 8,724,100 B1 | 5/2014 | Asghari et al. |
| 8,792,869 B2 | 7/2014 | Prentice et al. |
| 8,873,026 B2 | 10/2014 | Puig |
| 8,920,332 B2 | 12/2014 | Hong et al. |
| 8,948,832 B2 | 2/2015 | Hong et al. |
| 8,983,250 B2 | 3/2015 | Black et al. |
| 9,020,004 B2 | 4/2015 | Jeong |
| 9,028,123 B2 * | 5/2015 | Nichol ............... G02B 6/0028 362/616 |
| 9,031,412 B2 | 5/2015 | Nagarajan |
| 9,039,614 B2 | 5/2015 | Yuen et al. |
| 9,049,998 B2 | 6/2015 | Brumback et al. |
| 9,066,691 B2 | 6/2015 | Addison et al. |
| 9,091,715 B2 | 7/2015 | Alameh et al. |
| 9,110,259 B1 | 8/2015 | Black |
| 9,135,397 B2 | 9/2015 | Denyer et al. |
| 9,176,282 B2 | 11/2015 | Pottier |
| 9,217,669 B2 | 12/2015 | Wu et al. |
| 9,237,855 B2 | 1/2016 | Hong et al. |
| 9,241,635 B2 | 1/2016 | Yuen et al. |
| 9,274,507 B2 | 3/2016 | Kim et al. |
| 9,314,197 B2 | 4/2016 | Eisen et al. |
| 9,348,154 B2 | 5/2016 | Hayakawa |
| 9,360,554 B2 | 6/2016 | Retterath et al. |
| 9,370,689 B2 | 6/2016 | Guillama et al. |
| 9,392,946 B1 | 7/2016 | Sarantos |
| 9,405,066 B2 | 8/2016 | Mahgerefteh |
| 9,423,418 B2 | 8/2016 | Alameh et al. |
| 9,510,790 B2 | 12/2016 | Kang et al. |
| 9,513,321 B2 | 12/2016 | Frangen |
| 9,515,378 B2 | 12/2016 | Prasad |
| 9,526,421 B2 | 12/2016 | Papadopoulos et al. |
| 9,526,433 B2 | 12/2016 | Lapelina et al. |
| 9,543,736 B1 | 1/2017 | Barwicz et al. |
| 9,558,336 B2 | 1/2017 | Lee |
| 9,603,569 B2 | 3/2017 | Mirov et al. |
| 9,620,931 B2 | 4/2017 | Tanaka |
| 9,643,181 B1 | 5/2017 | Chang |
| 9,766,370 B2 | 9/2017 | Aloe et al. |
| 9,782,128 B2 | 10/2017 | Lee et al. |
| 9,784,829 B2 | 10/2017 | Zeng |
| 9,804,027 B2 | 10/2017 | Fish et al. |
| 9,829,631 B2 | 11/2017 | Lambert |
| 9,833,179 B2 | 12/2017 | Ikeda |
| 9,861,286 B1 | 1/2018 | Islam |
| 9,875,560 B2 | 1/2018 | Rajagopalan |
| 9,880,352 B2 | 1/2018 | Florjanczyk |
| 9,943,237 B2 | 4/2018 | Baker et al. |
| 9,946,020 B1 | 4/2018 | Horth |
| 9,948,063 B2 | 4/2018 | Caneau et al. |
| 9,952,433 B2 | 4/2018 | Um et al. |
| 9,974,466 B2 | 5/2018 | Kimmel |
| 10,009,668 B2 | 6/2018 | Liboiron-Ladouceur |
| 10,016,613 B2 | 7/2018 | Kavounas et al. |
| 10,132,996 B2 | 11/2018 | Lambert |
| 10,136,859 B2 | 11/2018 | Cutaia |
| 10,181,021 B2 | 1/2019 | Verkatraman et al. |
| 10,188,330 B1 | 1/2019 | Kadlec et al. |
| 10,203,454 B2 | 2/2019 | Liu |
| 10,238,351 B2 | 3/2019 | Halperin et al. |
| 10,243,684 B2 | 3/2019 | Wen |
| 10,271,745 B2 | 4/2019 | Gu et al. |
| 10,278,591 B2 | 5/2019 | Gil |
| 10,285,898 B2 | 5/2019 | Douglas et al. |
| 10,310,196 B2 | 6/2019 | Hutchison |
| 10,317,200 B1 | 6/2019 | Han et al. |
| 10,372,160 B2 | 8/2019 | Lee et al. |
| 10,376,164 B2 | 8/2019 | Presura et al. |
| 10,429,597 B2 | 10/2019 | ten Have et al. |
| 10,444,067 B2 | 10/2019 | Hsu et al. |
| 10,529,003 B2 | 1/2020 | Mazed |
| 10,537,270 B2 | 1/2020 | Sarussi et al. |
| 10,559,708 B2 | 2/2020 | Chua |
| 10,599,192 B2 | 3/2020 | Younes et al. |
| 10,610,157 B2 | 4/2020 | Pandya et al. |
| 10,645,470 B2 | 5/2020 | Baxi et al. |
| 10,646,145 B2 | 5/2020 | Pekander et al. |
| 10,702,211 B2 | 7/2020 | Clavelle et al. |
| 10,705,211 B2 | 7/2020 | Jacobs et al. |
| 10,741,064 B2 | 8/2020 | Schwarz et al. |
| 10,795,508 B2 | 10/2020 | Han et al. |
| 10,799,133 B2 | 10/2020 | Lee |
| 10,806,386 B2 | 10/2020 | Lobbestael et al. |

(56) References Cited

U.S. PATENT DOCUMENTS

| | | |
|---|---|---|
| 10,843,066 B2 | 11/2020 | Nicoli |
| 10,852,492 B1 | 12/2020 | Vermeulen et al. |
| 10,874,348 B1 | 12/2020 | Han et al. |
| 10,996,399 B2 | 5/2021 | Yang et al. |
| 11,076,769 B2 | 8/2021 | Lee |
| 11,145,310 B2 | 10/2021 | Sakurai |
| 11,190,556 B2 | 11/2021 | Meiyappan et al. |
| 11,224,381 B2 | 1/2022 | McHale et al. |
| 11,255,663 B2 | 2/2022 | Binder |
| 11,309,929 B2 | 4/2022 | Wong |
| 11,511,440 B2 | 11/2022 | Polanco et al. |
| 11,857,298 B1 | 1/2024 | Allec et al. |
| 2002/0029128 A1 | 3/2002 | Jones et al. |
| 2005/0053112 A1 | 3/2005 | Shams-Zadeh-Amiri |
| 2005/0063431 A1 | 3/2005 | Gallup et al. |
| 2006/0002443 A1 | 1/2006 | Farber et al. |
| 2006/0253010 A1 | 11/2006 | Brady et al. |
| 2008/0044128 A1 | 2/2008 | Kish et al. |
| 2008/0310470 A1 | 12/2008 | Ooi et al. |
| 2010/0158067 A1 | 6/2010 | Nakatsuka et al. |
| 2012/0119920 A1 | 5/2012 | Sallop et al. |
| 2012/0310062 A1 | 12/2012 | Li et al. |
| 2013/0030267 A1 | 1/2013 | Lisogurski et al. |
| 2014/0029943 A1 | 1/2014 | Mathai et al. |
| 2014/0069951 A1 | 3/2014 | Schmidt et al. |
| 2014/0073968 A1 | 3/2014 | Engelbrecht et al. |
| 2015/0164352 A1 | 6/2015 | Yoon et al. |
| 2016/0129279 A1 | 5/2016 | Ferolito |
| 2016/0224750 A1 | 8/2016 | Kethman et al. |
| 2016/0296174 A1 | 10/2016 | Isikman et al. |
| 2017/0115825 A1 | 4/2017 | Eriksson et al. |
| 2017/0135633 A1 | 5/2017 | Connor |
| 2017/0164878 A1 | 6/2017 | Connor |
| 2017/0325698 A1 | 11/2017 | Allec et al. |
| 2017/0347902 A1 | 12/2017 | Van Gool et al. |
| 2018/0014785 A1 | 1/2018 | Li |
| 2018/0073924 A1 | 3/2018 | Steinmann et al. |
| 2018/0227754 A1 | 8/2018 | Paez Velazquez |
| 2019/0015045 A1 | 1/2019 | Li |
| 2019/0069781 A1 | 3/2019 | Kim et al. |
| 2019/0083034 A1 | 3/2019 | Shim et al. |
| 2019/0339468 A1 | 11/2019 | Evans et al. |
| 2019/0342009 A1 | 11/2019 | Evans et al. |
| 2020/0085374 A1 | 3/2020 | Lin et al. |
| 2020/0152615 A1 | 5/2020 | Krasulick et al. |
| 2020/0244045 A1 | 7/2020 | Bismuto et al. |
| 2020/0253547 A1 | 8/2020 | Harris et al. |
| 2020/0297955 A1 | 9/2020 | Shouldice |
| 2020/0309593 A1 | 10/2020 | Bismuto et al. |
| 2021/0033805 A1 | 2/2021 | Bishop et al. |
| 2021/0194481 A1 | 6/2021 | Rademeyer et al. |
| 2022/0011157 A1 | 1/2022 | Bismuto et al. |
| 2022/0059992 A1 | 2/2022 | Hill et al. |
| 2022/0075036 A1 | 3/2022 | Zhou et al. |
| 2022/0091333 A1 | 3/2022 | Wu |
| 2022/0099896 A1 | 3/2022 | Arbore et al. |
| 2023/0190167 A1 | 6/2023 | Jung |
| 2023/0404419 A1 | 12/2023 | Allec et al. |

FOREIGN PATENT DOCUMENTS

| | | |
|---|---|---|
| EP | 3561561 | 10/2019 |
| FR | 2949024 | 2/2011 |
| JP | S60127776 | 7/1985 |
| JP | S63177495 | 7/1988 |
| JP | 2000163031 | 6/2000 |
| JP | 2002342033 | 11/2002 |
| JP | 2008262118 | 10/2008 |
| WO | WO 01/014929 | 3/2001 |
| WO | WO 02/011339 | 2/2002 |
| WO | WO 04/031824 | 4/2004 |
| WO | WO 05/091036 | 9/2005 |
| WO | WO 11/090274 | 7/2011 |
| WO | WO 15/051253 | 4/2015 |
| WO | WO 15/094378 | 6/2015 |
| WO | WO 15/105881 | 7/2015 |
| WO | WO 17/040431 | 3/2017 |
| WO | WO 17/184420 | 10/2017 |
| WO | WO 17/184423 | 10/2017 |
| WO | WO 19/152990 | 8/2019 |
| WO | WO 20/106974 | 5/2020 |

OTHER PUBLICATIONS

U.S. Appl. No. 17/254,810, filed Dec. 21, 2020, Bishop et al.

Gonzalez-Sanchez et al., "Capacitive Sensing for Non-Invasive Breathing and Heart Monitoring in Non-Restrained, Non-Sedated Laboratory Mice," Sensors 2016, vol. 16, No. 1052, pp. 1-16.

Kybartas et al., "Capacitive Sensor for Respiratory Monitoring," Conference "Biomedical Engineering," Nov. 2015, 6 pages.

Lapedus, "Electroplating IC Packages—Tooling challenges increase as advanced packaging ramps up," *Semiconductor Engineering*, https://semiengineering.com/electroplating-ic-packages, Apr. 10, 2017, 22 pages.

Materials and Processes for Electronic Applications, Series Editor: James J. Licari, AvanTeco, Whittier, California, Elsevier Inc., 2009, 20 pages.

Worhoff et al., "Flip-chip assembly for photonic circuits," MESA+ Research Institute, University of Twente, Integrated Optical MicroSystems Group, The Netherlands, 12 pages.

He et al., "Integrated Polarization Compensator for WDM Waveguide Demultiplexers," IEEE Photonics Technology Letters vol. 11, No. 2, Feb. 1999, pp. 224-226.

\* cited by examiner

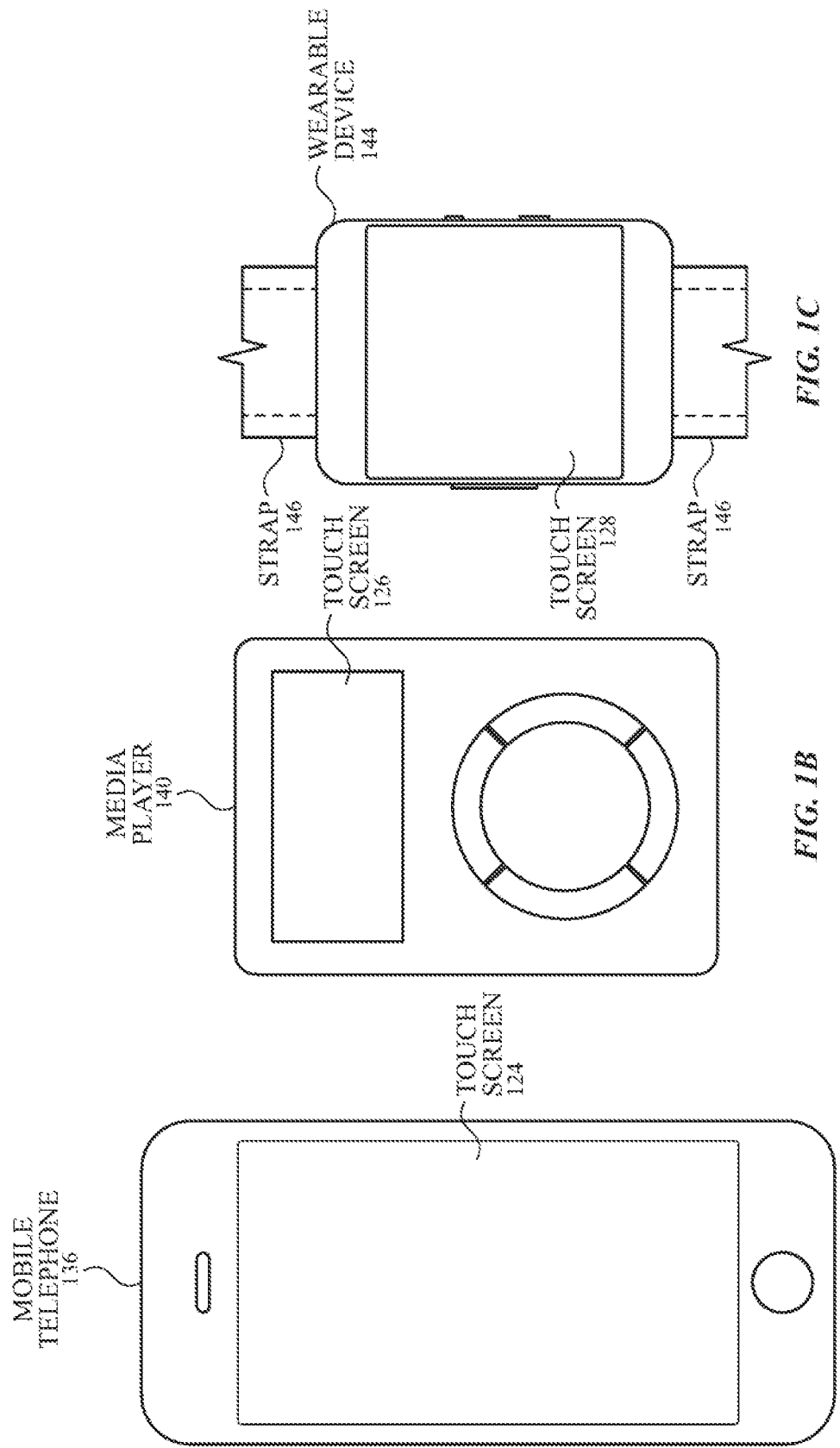

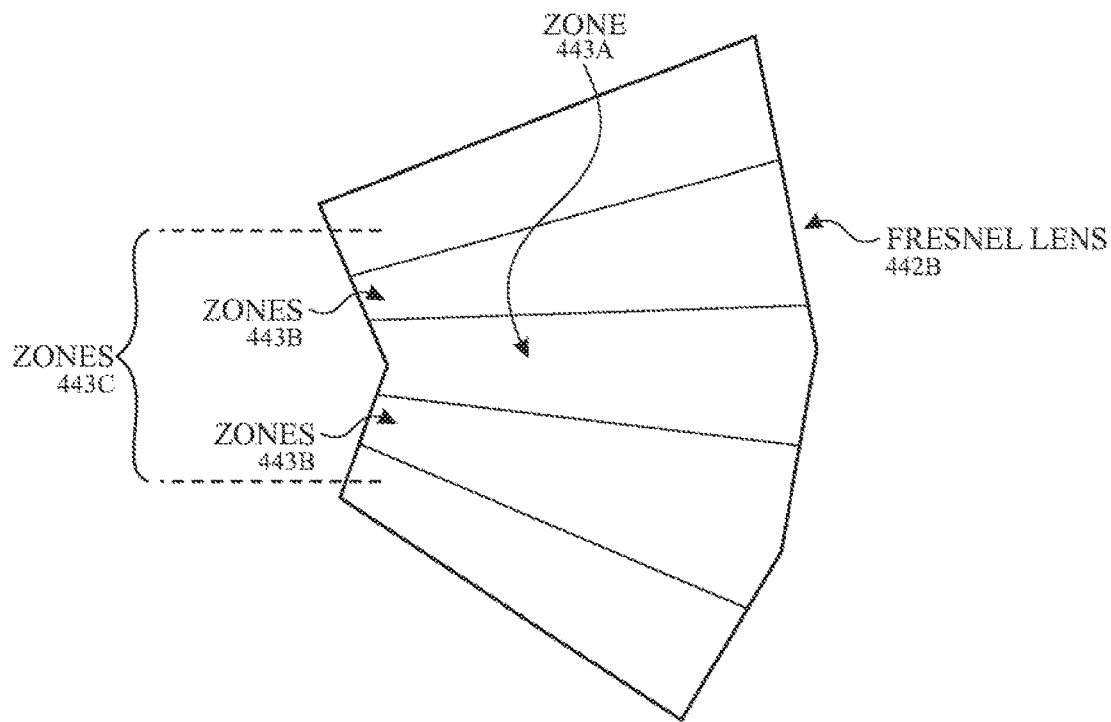
*FIG. 4D*
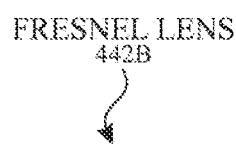
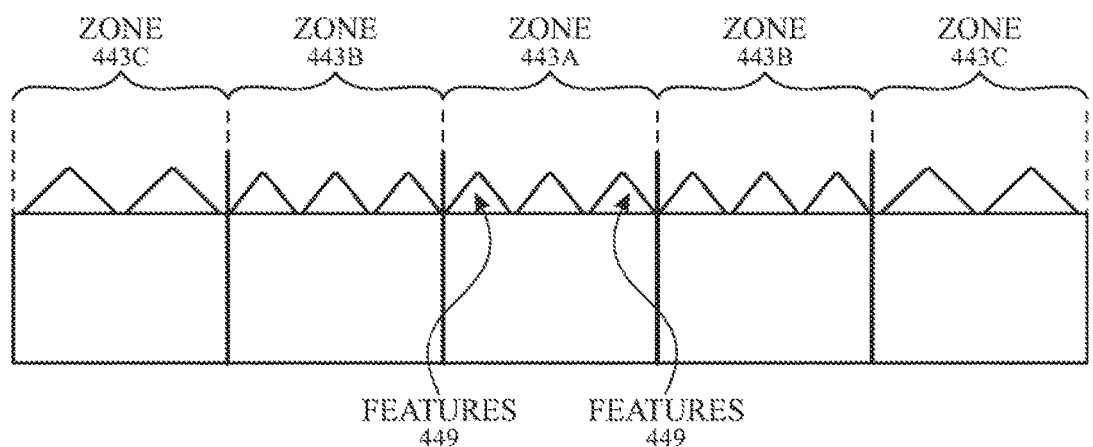
*FIG. 4E*

SYSTEMS AND METHODS FOR DISTINGUISHING BETWEEN A USER AND AN OBJECT

CROSS-REFERENCE TO RELATED APPLICATION

This application is a nonprovisional of and claims the benefit under 35 U.S.C. § 119(e) to U.S. Provisional Patent Application No. 62/736,270, filed Sep. 25, 2018, and entitled "Systems and Methods for Distinguishing Between a User and an Object," the contents of which are incorporated herein by reference as if fully disclosed herein.

FIELD

This disclosure relates generally to optical sensing units, and more particularly to optical sensing units configured for distinguishing between a user's body (e.g., wrist) and an object (e.g., table surface, watch band, etc.).

BACKGROUND

Optical sensing units can be used to measure photoplethysmogram (PPG) signals and corresponding systems can use the signals to derive related physiological signals (e.g., pulse rate). In a basic form, the optical sensing unit can include a light emitter that emits light through an aperture and/or window into the user's tissue. In addition, a light detector can be included to receive light through an aperture and/or window. The light received by the light detector can be light that has returned (e.g., reflected off) and exited the tissue. The optical sensing unit can be included in a wearable device, such as a watch.

In some instances, the wearable device may not be proximate to the user's body and may instead be proximate to an object. The light received by the light detector can be light that has returned from this other object. Some optical sensing units may not be able to distinguish between return light from the user's tissue and return light from an object, which may result in inaccurate measurements. The measurements may be used for conditional operation of one or more other processes and/or components, where inaccurate measurements may erroneously trigger the other processes, operation of the components, or both.

SUMMARY

Disclosed herein is an electronic device including an optical sensing unit configured for distinguishing between a user's body and an object. The optical sensing unit can include a plurality of light detectors, a plurality of first light emitters, and a plurality of second light emitters. The plurality of first light emitters can be configured for measuring physiological information of the user, and the plurality of second light emitters can be configured for measuring a state of the device. The device can include one or more optical components, which can allow the plurality of second light emitters to emit first light towards the strap attached to the device and second light towards the edge of the device (e.g., not incident on the strap of the device). In some examples, the plurality of second light emitters can include a third light emitter and corresponding optical component(s) to emit third light, where the second light can be emitted towards one edge (e.g., right) of the device, and the third light can be emitted towards another edge (e.g., left) of the device. The plurality of light detectors can measure return light from the first, second, and/or third light to determine one or more states of the device. Exemplary states of a device can include the device being on-wrist and the device being off-wrist. The device may also have one or more sub-states included in a state. As one example, the device may have a state of being off-wrist and a sub-state of resting on a surface (e.g., table, chair, etc.). As another example, the device may have a state of being on-wrist and a sub-state of being oriented in a tilted configuration relative to the user's body.

BRIEF DESCRIPTION OF THE DRAWINGS

FIGS. 1A-1C illustrate systems in which examples of the disclosure can be implemented.

FIGS. 4D-4E illustrate top and cross-sectional views of an exemplary Fresnel lens including multiple regions according to examples of the disclosure.

DETAILED DESCRIPTION

Figure 2A:
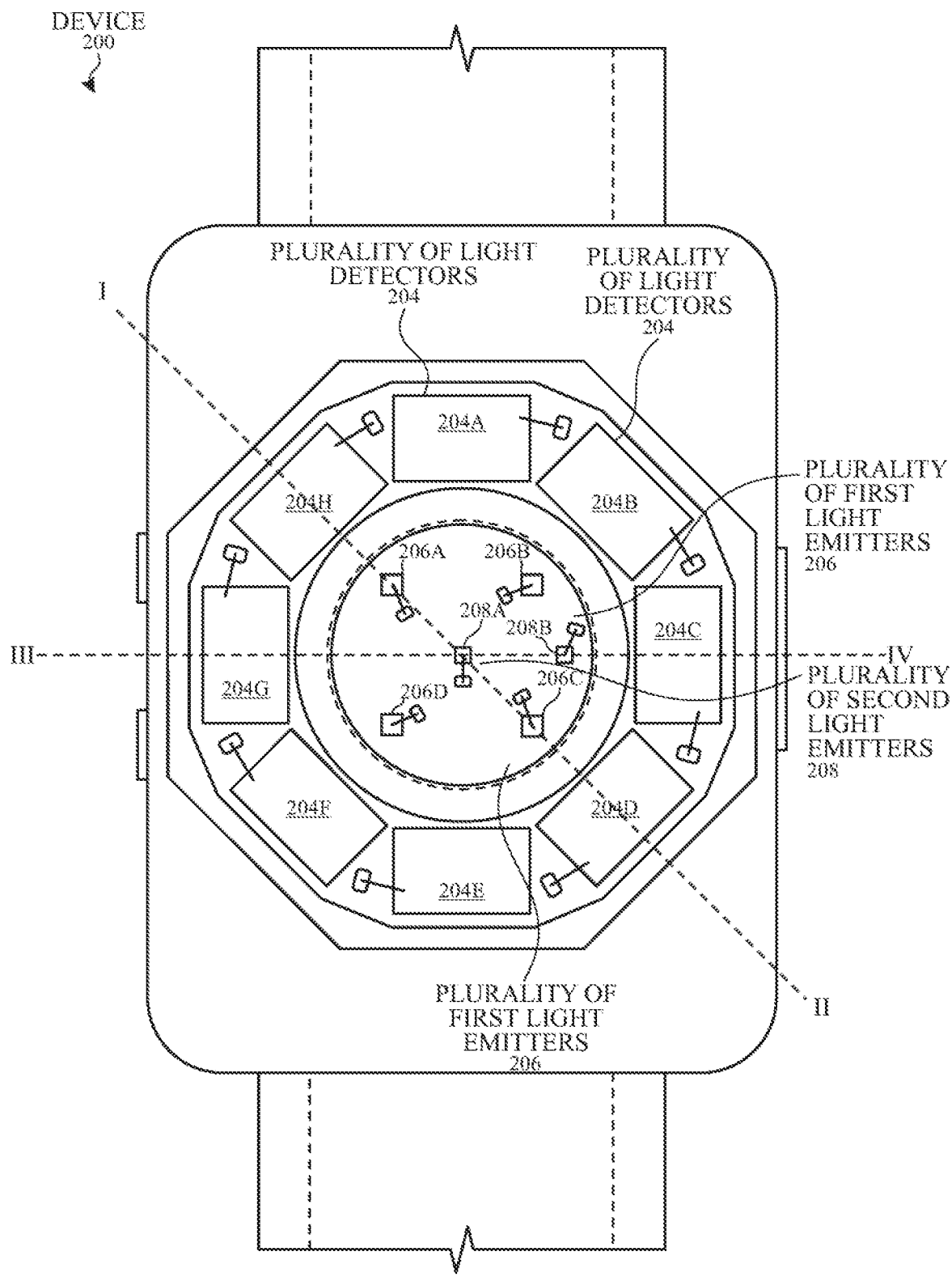
FIG. 2A illustrates a top view of an exemplary electronic device including a concentric architecture for optical sensing according to examples of the disclosure.

In the following description of examples, reference is made to the accompanying drawings in which it is shown by way of illustration specific examples that can be practiced. It is to be understood that other examples can be used and structural changes can be made without departing from the scope of the various examples. Numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Optical sensing units can be used to measure photoplethysmogram (PPG) signals and corresponding systems can use the signals to derive related physiological signals (e.g., pulse rate). In a basic form, the optical sensing unit can include a light emitter that emits light through an aperture and/or window into the user's tissue. In addition, a light detector can be included to receive light through an aperture and/or window. The light received by the light detector can be light that has returned (e.g., reflected off) and exited the tissue. The optical sensing unit can be included in a wearable device, such as a watch.

In some instances, the wearable device may not be proximate to the user's body and may instead be proximate to an object. The light received by the light detector can be light that has returned from this object. Some optical sensing units may not be able to distinguish between return light from the user's tissue and return light from an object, which may result in inaccurate measurements. The measurements may be used for conditional operation of one or more other processes and/or components, where inaccurate measurements may erroneously trigger the other processes, operation of the components, or both.

In some examples, the optical sensing unit can be included in a device, and the optical sensing unit configured to determine the state of a device. Exemplary states of a device can include the device being on-wrist and the device being off-wrist. A device can be on-wrist when it is proximate (e.g., secured) to a user's skin, or can otherwise be off-wrist. The device may also have one or more sub-states included in a state. As one example, the device may have a state of being off-wrist and a sub-state of resting on a surface (e.g., table, chair, etc.). As another example, the device may have a state of being on-wrist and a sub-state of being oriented in a tilted configuration relative to the user's body. As discussed in detail below, the device can assign one or more confidence levels to a given state, sub-state, or both. The confidence level can be a value indicative of the confidence that the device has the respective state or sub-state.

The different states and sub-states of the device can be used for conditional operation of one or more other processes and/or components. Exemplary operations when the device is off-wrist can include ignoring PPG signals to improve the measurement accuracy, powering off one or more components to reduce power consumption, requiring a password to prevent access to the device for enhanced security, and others. To determine whether a device is on-wrist or off-wrist, the optical sensing unit can include at least one light emitter-light detector pair. The light emitter can be configured to emit light of a certain wavelength (e.g., infrared wavelengths), and the light detector can be configured, at least in part, to detect the same wavelength. When one or more criteria are met, the processor included in the device can determine the state of the device. For example, the criteria can include the light detector detecting light of the same wavelength and having an intensity within a given range (e.g., indicative of values related to human skin), and in response to meeting this criteria, the processor can determine that the device is on-wrist.

The device may determine that it is off-wrist when the light detectors do not detect light of the same wavelength and having an intensity within the given range. For example, the device may attach to the user by way of a strap. In some instances, the strap may include a clasp that fastens two portions of the strap together. There may be a moment in time (e.g., when the user removes the device from his or her wrist) where the two portions may not be fastened together, so the emitted light may not reflect back to the light detector.

In some instances, the device may erroneously determine that the device is on-wrist even though it may not be. For example, the strap may be a continuous strap having a single portion that may cause the emitted light to reflect back to the light detector even when the device may not proximate to the user.

Disclosed herein is an electronic device including an optical sensing unit configured for distinguishing between a user's body and an object. The optical sensing unit can include a plurality of light detectors, a plurality of first light emitters, and a plurality of second light emitters. The plurality of first light emitters can be configured for measuring physiological information of the user, and the plurality of second light emitters can be configured for measuring a state of the device. The device can include one or more optical components, which can allow the plurality of second light emitters to emit first light towards the strap attached to the device and second light towards the edge of the device (e.g., not incident on the strap of the device). In some examples, the plurality of second light emitters can include a third light emitter and corresponding optical component(s) to emit third light, where the second light can be emitted towards one edge (e.g., right) of the device, and the third light can be emitted towards another edge (e.g., left) of the device. The plurality of light detectors can measure return light from the first, second, and/or third light to determine one or more states of the device. Exemplary states of a device can include the device being on-wrist and the device being off-wrist. The device may also have one or more sub-states included in a state. As one example, the device may have a state of being off-wrist and a sub-state of resting on a table. As another example, the device may have a state of being on-wrist and a sub-state of being oriented in a tilted configuration relative to the user's body.

Representative applications of the apparatus and methods according to the present disclosure are described in this section. These examples are being provided solely to add context and aid in the understanding of the described examples. It will thus be apparent to one skilled in the art that the described examples may be practiced without some or all of the specific details. Other applications are possible, such that the following examples should not be taken as limiting.

Exemplary Systems

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the optical sensing unit and/or methods for determining the state of the device, as will be disclosed.

Overview of the Optical Sensing Unit

The optical sensing unit can be arranged in any configuration including, but not limited to, a concentric configuration. FIG. 2A illustrates a top view of an exemplary electronic device including a concentric architecture for optical sensing according to examples of the disclosure. The top view in FIG. 2A can be viewed as the underside of wearable device 144 of FIG. 1C, for example. Further, the top view in FIG. 2A includes a partial top view of the device.

Device 200 can include a plurality of light detectors 204A, 204B, 204C, 204D, 204E, 204F, 204G, and 204H (collectively referred to as plurality of light detectors 204); a plurality of first light emitters 206A, 206B, 206C, and 206D (collectively referred to as plurality of first light emitters 206); and a plurality of second light emitters 208A and 208B (collectively referred to as plurality of second light emitters 208). The device 200 can be situated such that the plurality of light detectors 204, the plurality of first light emitters 206, and the plurality of second light emitter 208 are proximate to a user's skin. For example, the device 200 can be held in a user's hand or strapped to a user's wrist, among other possibilities. In some examples, the plurality of first light emitters 206 can be configured to emit a different range(s) of wavelengths (e.g., green wavelengths) than the plurality of second light emitters 208 (e.g., infrared wavelengths).

The plurality of first light emitters 206 can be configured for one or more physiological measurements, and the plurality of second light emitters 208 can be configured for determining one or more states of the device 200, as discussed below. The plurality of light detectors 204 can be configured to measure return light from the plurality of first light emitters 206, from the plurality of second light emitters 208, or both. In some examples, one set of the plurality of light detectors 204 can be configured for physiological measurements, and another set of the plurality of light detectors 204 can be configured for determining the state of the device 200.

Figure 2B:
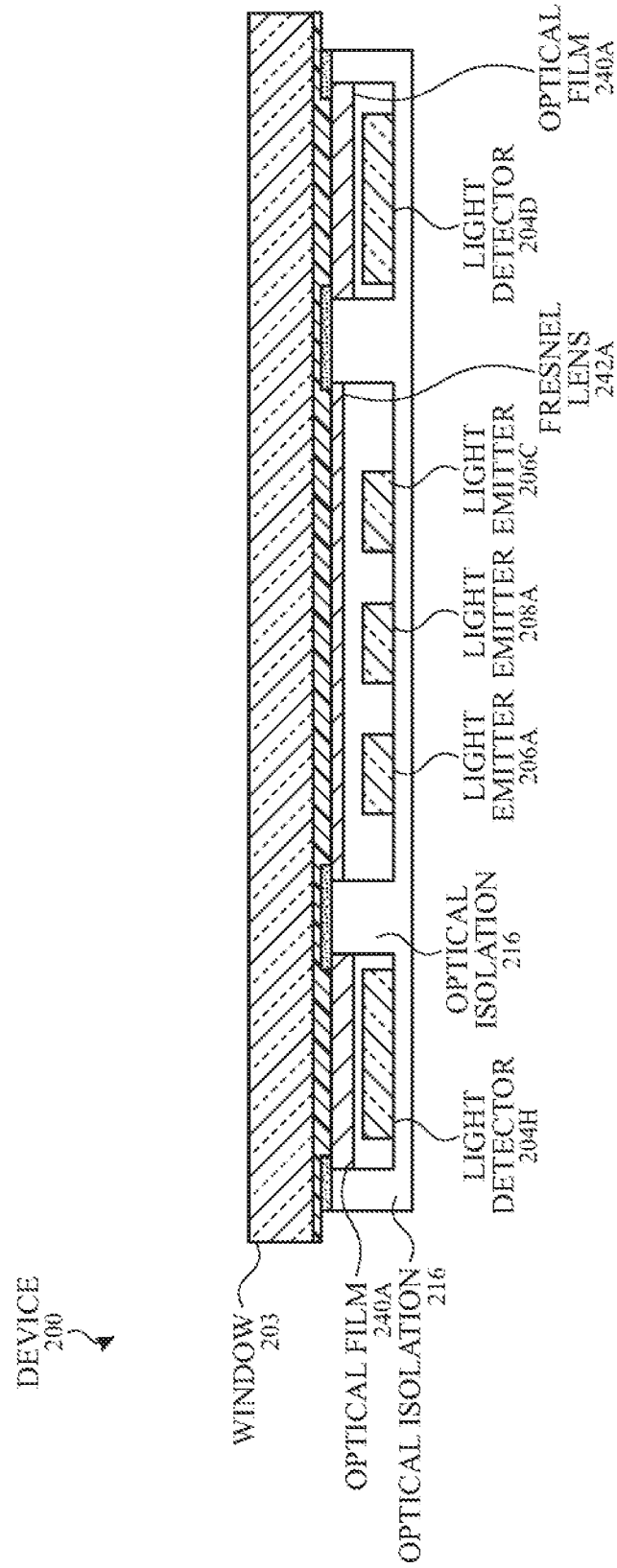
FIG. 2B illustrates the cross-sectional view of FIG. 2A along line I-II according to examples of the disclosure.

The device 200 can include one or more additional optical components. The additional optical components can be used for one or more functions, such as enhancing optical collection, enhancing signal generation, reducing noise, and the like. FIG. 2B illustrates a cross-sectional view of FIG. 2A along line I-II. The one or more components can include optical isolation 216, one or more optical films 240A, and a Fresnel lens 242A. The optical isolation 216 can be a wall located between the plurality of light detectors 204 and the plurality of first light emitters 206 used to prevent or reduce optical crosstalk between the plurality of light detectors 204 and the light emitters. The optical isolation 216 may form at least two cavities in which the light emitters and light detectors may be located within. Other types of isolation may include, but are not limited to, optical, electrical, and/or mechanical isolation of the optical sensing unit from other components (e.g., a display or a touch screen) included in the device.

The optical film 240A can be a film configured for changing the properties of light (e.g., light restriction, light steering, etc.). The optical film 240A can at least partially overlay (i.e., is located in the line of sight of) a section of window 203 that corresponds to light passing through to at least one light detector 204. In some examples, the device 200 can include one section of the optical film 240A disposed over (i.e., in the path of light emitted by) each light detector 204. The optical film 240A can have other arrangements such as being attached to a window 203, being disposed on a window, being disposed on a detector, and the like. In some examples, a single (e.g., ring-shaped) optical film 240A can be disposed over a plurality (including all) of the light detectors 204. In some examples, the edges of the optical film 240A can extend to (e.g., contact) the optical isolation 216.

The Fresnel lens 242A can be a lens configured to direct and/or focus light emitted by one or more light emitters. The Fresnel lens 242A can at least partially overlay a section of the window 203 corresponding to light passing through from the plurality of first light emitters 206 and/or the second light emitter(s) 208. In some examples, the Fresnel lens 242A can be configured for obscuration of the light emitters. For example, the features of the Fresnel lens 242A can be based on achieving optimal measurements associated with the second light emitter 208 and associated with the plurality of first light emitters 206, while also reducing the visibility of the light emitters.

Overview Operation of the Optical Sensing Unit

Figure 2C:
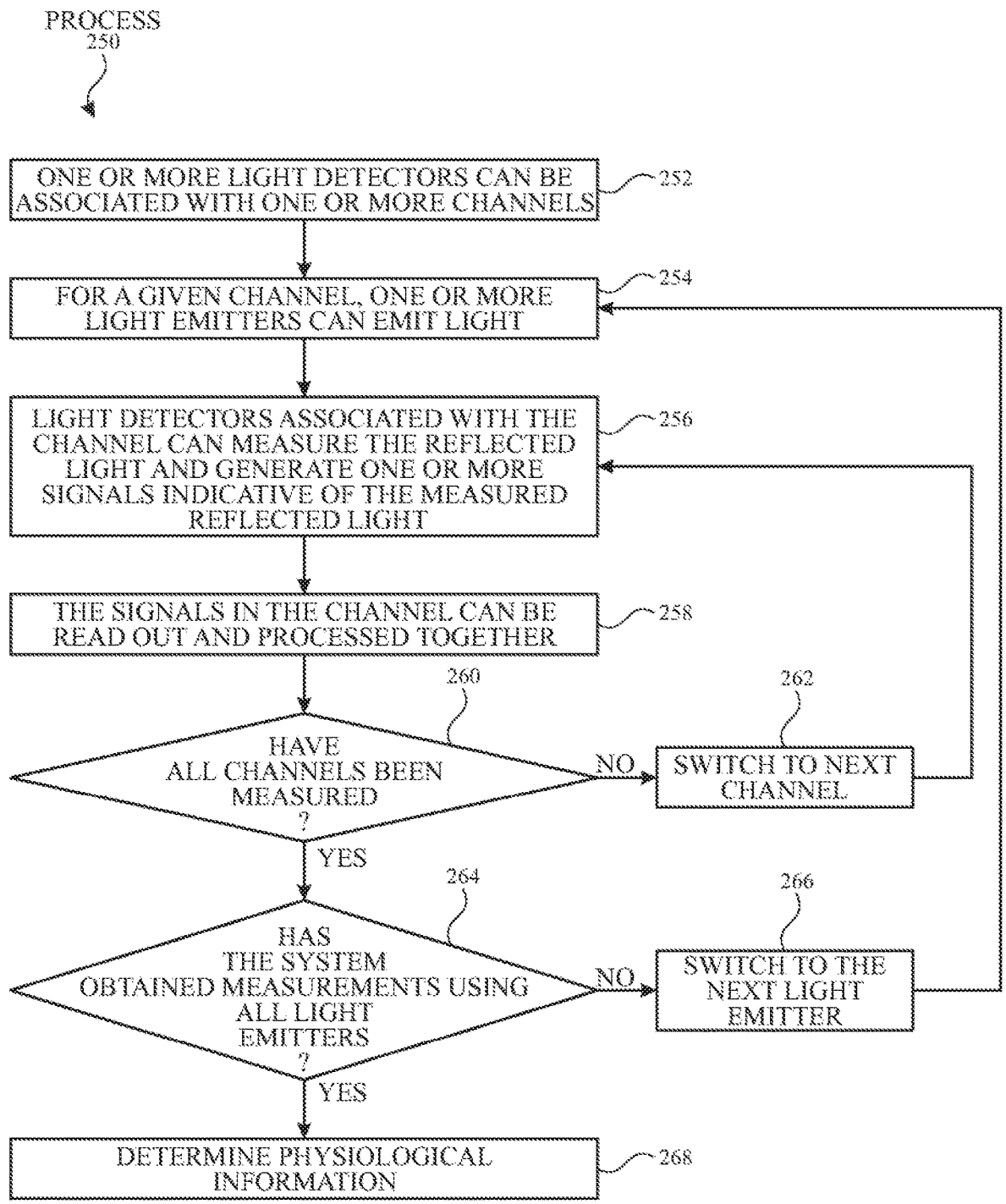
FIG. 2C illustrates an exemplary process flow for operating the optical sensing unit to measure one or more physiological signals according to examples of the disclosure.

The sensing unit can be operated to measure one or more physiological signals. FIG. 2C illustrates an exemplary process flow for operating the optical sensing unit to measure one or more physiological signals according to examples of the disclosure. One or more light detectors (e.g., all of the plurality of light detectors 204) can be associated with one or more channels (step 252 of process 250). In some examples, the channels can be dynamically (i.e., in real-time) changed based on the selected first light emitter 206. In some examples, the channels can be dynamically changed based on the spacing. For a given channel, one or more light emitters (e.g., first light emitter 206) can emit light (e.g., green light) (step 254 of process 250). A portion of the light can be absorbed by the user's skin, vasculature, and/or blood, and a portion of the light can return to the light detectors. The light detector(s) associated with the given channel can measure the return light and generate one or more signals indicative of the measured return light (step 256 of process 250). The signals in the channel may be read out and processed (e.g., summed) together, for example, to produce a channel signal (step 258 of process 250). The processor can measure channels sequentially or concurrently. In situations where the channels are measured sequentially, the process can be repeated for other channels until some or all channels are measured for a given light emitter. In some examples, multiple (including all) channels may be readout simultaneously, where signals within the same channel can be processed separately from signals from other channels. Another light emitter (e.g., first light emitter 206A) can be selected for the measurements (step 264 and step 266 of process 250). Measuring multiple light emitters can allow the system to measure multiple regions of the user's skin for enhanced measurement accuracy. From the signals, the physiological information can be determined (step 268 of process 250).

The optical sensing unit can also be configured for determining the state of the device using any number of the exemplary configurations and/or methods given below.

Exemplary Device Configuration and Operation for Multiple Split Light Beams

Figure 3A:
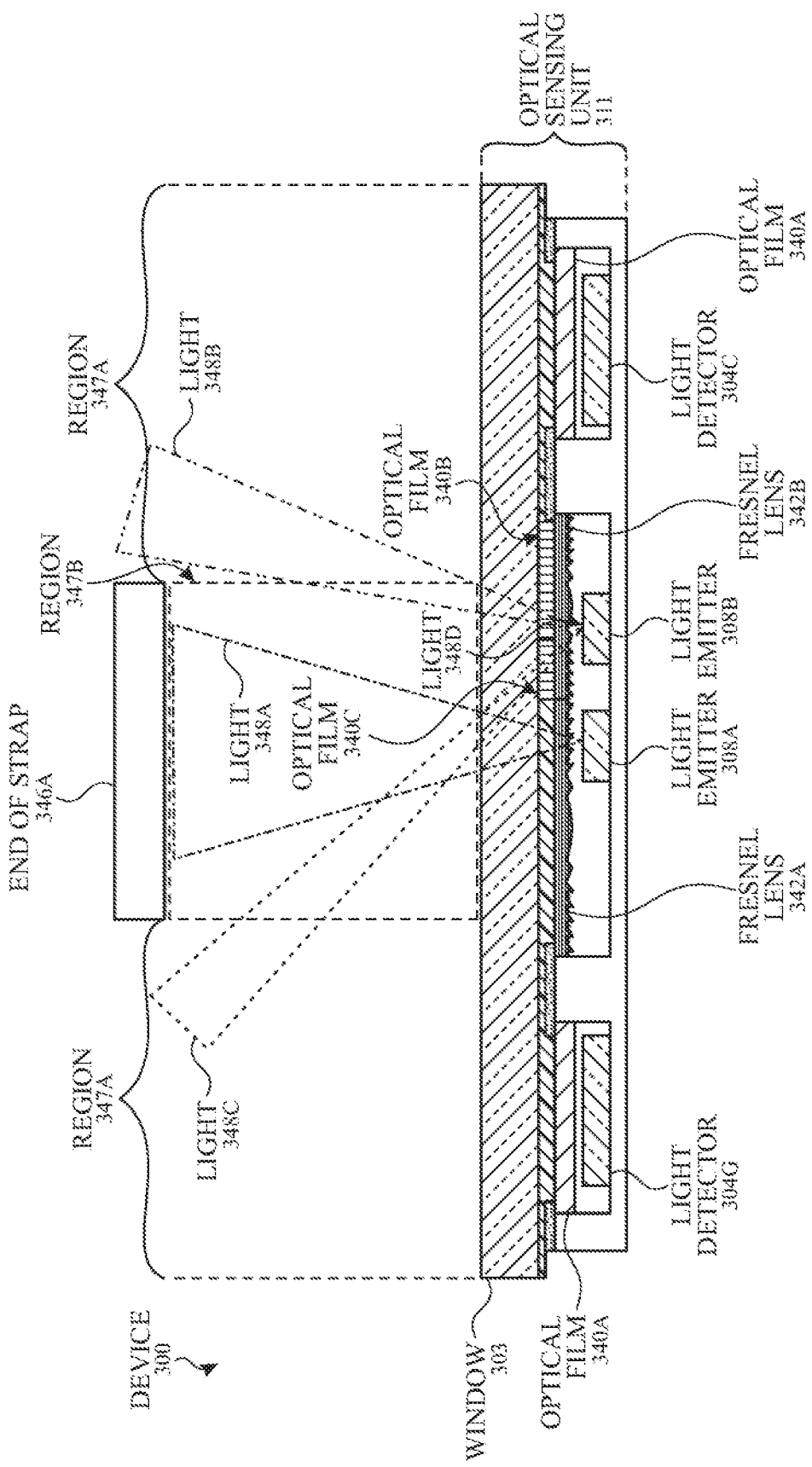
FIG. 3A illustrates a cross-sectional view of FIG. 2A along line III-IV.

In some examples, the optical sensing unit can be configured to determine whether the state of the device, specifically whether the device is on-wrist or off-wrist. A device can be on-wrist when it is proximate (e.g., secured) to a user's skin, or can otherwise be off-wrist. FIG. 3A illustrates a cross-sectional view of FIG. 2A along line III-IV. Device 300 can include an optical sensing unit 311. The optical sensing unit 311 can include a plurality of light detectors 304, a plurality of first light emitters 306, a window 303, optical films 340A, and a Fresnel lens 342A, which may be correspondingly similar to the plurality of light detectors 204, the plurality of first light emitters 206, the window 203, the optical films 240A, and the Fresnel lens 242A. Additionally, the device 300 may include one or more components (not shown) such as an optical isolation and/or may be similarly configured as device 200. The device 300 may also include a plurality of second light emitters 308, which may be correspondingly similar to the plurality of second light emitters 208.

The plurality of second light emitters 308 can be configured to emit two independent light beams for detecting an off-wrist state. The second light emitter 308A can emit a light 348A, and the second light emitter 308B can emit light 348D. The second light emitter 308A may be configured such that light 348A is a center light beam directed towards an object, such as the end of the strap 346A. In some examples, the second light emitter 308B can be configured such that light 348D is a light beam directed towards the window 303.

Figure 3B:
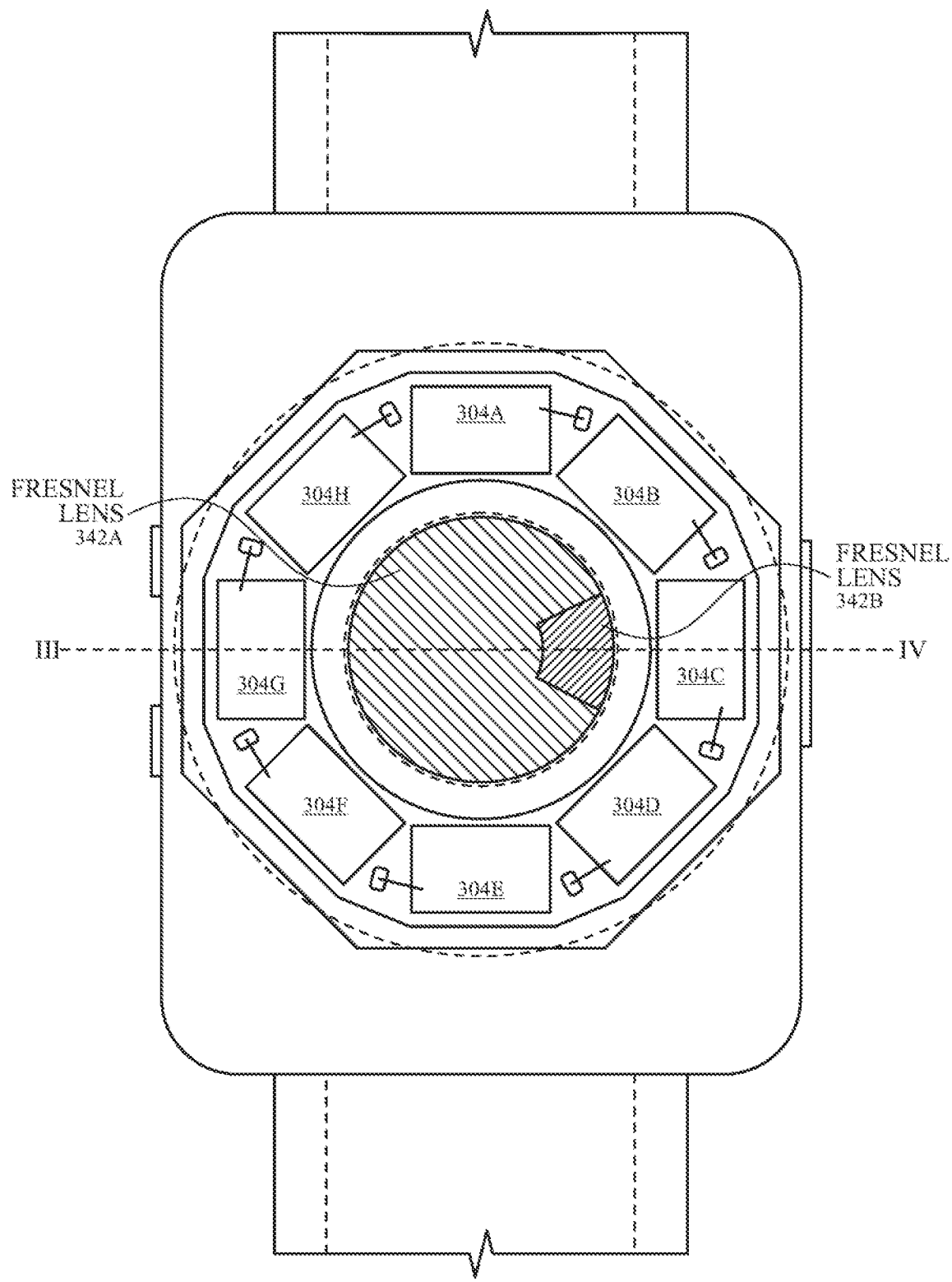
FIG. 3B illustrates a top view of the device including a Fresnel lens having multiple regions or multiple Fresnel lenses overlaying the light emitters according to examples of the disclosure.

The device can also include one or more components (e.g., Fresnel lens) for splitting light. FIG. 3B illustrates a top view of the device including one or more Fresnel lenses overlaying the light emitters according to examples of the disclosure. The device 300 can include at least two Fresnel lenses or a single Fresnel lens including multiple regions. Also referring to FIG. 3A, the Fresnel lens 342A may be located between the second light emitter 308A and the window 303 and can be configured to optimize the beam properties (e.g., shape, size, etc.) of light 348A. For example, the Fresnel lens 342A may, at least in part, shape light 348A such that it reaches the end of strap 346A and is not incident in regions 347A outside of strap 346. In some examples, the Fresnel lens 342A may also be located between one or more first light emitters (e.g., light emitter 206 illustrated in FIG. 2A) and the window 303. In other examples, a different Fresnel lens may be used for the first light emitters and the second light emitters.

The device 300 can also include a Fresnel lens 342B. The Fresnel lens 342B may be located between the second light emitter 308B and the window 303 and can be configured to create (e.g., split) separate light beams (light 348B and light 348C) from light 348D. In some examples, the Fresnel lens 342B can, alone or along with the optical films 340B and 340C, shape light 348B and light 348C such that they are directed towards regions 347A and do not reach the strap 346 (which includes the end of strap 346A), as shown in FIG. 3A. In some examples, the Fresnel lens 342B can include a single region having a plurality of features. The features may have the same properties (e.g., width, number of teeth, rounding, etc.) throughout.

The optical film 340B can be configured with one or more features (e.g., slats, light tubes, pipes, apertures, masks, etc.) for changing the angle of light 348B. The optical film 340C can be configured with one or more features for changing the angle of light 348C. Light 348B can be directed to one side (e.g., left side) of the strap 346, and light 348C can be directed to another side (e.g., right side) of the strap 346. In some examples, the one or more features of the optical film 340B may different from the one or more features of the optical film 340C.

In some examples, at least two of the second light emitters 308 can be located at different depths from the window 303. The depth of a given second light emitter 308 can be based on the targeted profile of its respective light beam. For example, light emitter 308A can be located further away from window 303 than light emitter 308B, which can cause light 348A to have a wider beam size at the end of strap 346A than light 348B has at the end of region 347A. The end of region 347A can have the same distance from window 303 as the end of strap 346A.

Figure 3C:
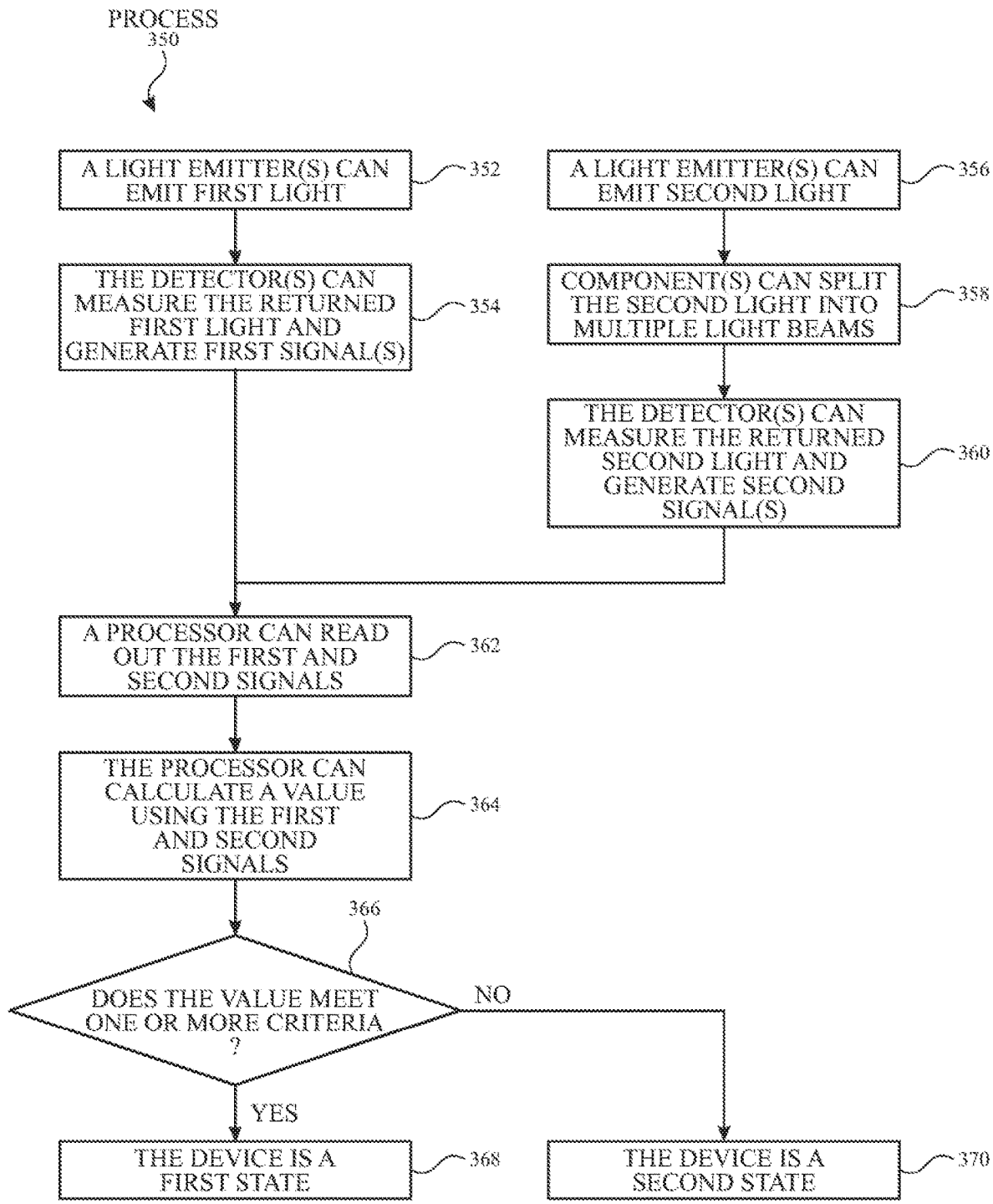
FIG. 3C illustrates an exemplary process flow for operating the optical sensing unit to determine the state of the device using multiple split light beams according to examples of the disclosure.

The device can be configured to use the multiple split light beams to determine the state of the device. FIG. 3C illustrates an exemplary process flow for operating the optical sensing unit to determine the state of the device using multiple split light beams according to examples of the disclosure. One or more light emitters (e.g., second light emitter 308A) can emit first light (e.g., infrared light 348A) (step 352 of process 350). If the device is on-wrist, then a portion of the first light can be absorbed by the user's skin, vasculature, and/or blood, and a portion of the first light can return to the light detectors (e.g., light detector 304G). If the device is off-wrist, then at least a portion of the first light can be incident on an object (e.g., strap 346) and can return to the light detectors. In some examples, the properties of the returned light can depend on the properties of the object. For example, objects having a darker color may absorb some of the light, leading to lower amount of light being returned. One or more detectors can measure the returned first light and generate one or more first signals indicative of the measured returned first light (step 354 of process 350).

One or more other light emitters (e.g., second light emitter 308B) can emit second light (e.g., infrared light 348D) (step 356 of process 350). One or more components(s) (e.g., Fresnel lens 342B, optical film 340B, optical film 340C, etc.) can be used to split the second light into multiple light beams (step 358 of process 350). If the device is on-wrist, then a portion of the second light can be absorbed by the user's skin, vasculature, and/or blood, and a portion of the second light can return to the light detectors. If the device is off-wrist, then the second light may not return to the light detectors or may return a signal indicative of the device being off-wrist. One or more detectors can measure the returned second light, if any, and can generate one or more second signals indicative of the measured returned second light (step 360 of process 350).

In some examples, step 352 and step 356 can occur concurrently, while one or more of steps 354, 358, and 360 can also occur concurrently or can be merged into a single step. For example, the first and second light emitters can emit first and second light concurrently. The second light can include one or more wavelengths unique from the first light, and the detectors can differentiate between the two light beams due to the different wavelengths.

A processor can read out the first and second signals (step 362 of process 350). The processor can determine one or more values using the first and second signals (step 364 of process 350). For example, the processor can divide the first signal(s) by the second signal(s) to lead to a value such as a ratio (step 364 of process 350). The processor can determine whether the value meets one or more criteria (e.g., is greater than a pre-determined threshold) (step 366 of process 350). If the value meets the criteria, then the processor can determine that the device is in a first state (step 368 of process 350). Otherwise, the processor can determine that the device is in a second state (step 370 of process 350). For example, if the ratio is greater than "1", then the processor can determine that the device is off-wrist. Otherwise, the processor can determine that the device is on-wrist.

Additionally or alternatively, the processor can determine the state based on differences in the first and second signals. For example, if the magnitudes of the first and second signals are similar (e.g., less than 10% difference), then the first and second signals can have uniform optical properties. The processor can determine that there is an object located in the region 347B between the end of the strap 346A and the optical sensing unit 311. As another example, if there is no object or a small object (e.g., one besides a user's wrist), the first and second signals may differ such that the first signal associated with light 348A may be higher than the second signal(s) associated with light 348B and/or light 348C. The differences in signals may be due to, e.g., a small object blocking some of light 348A, but not blocking light 348B, light 348C, or both.

One or more steps for determining the state of the device can occur concurrently or proximate in time with one or more other steps for measuring physiological signals. If the processor determines that the device is off-wrist, the processor may delay (or abort) another operation, such as measuring physiological signals, for example.

Exemplary Device Configuration for Multiple Independent Light Beams

Figure 4A:
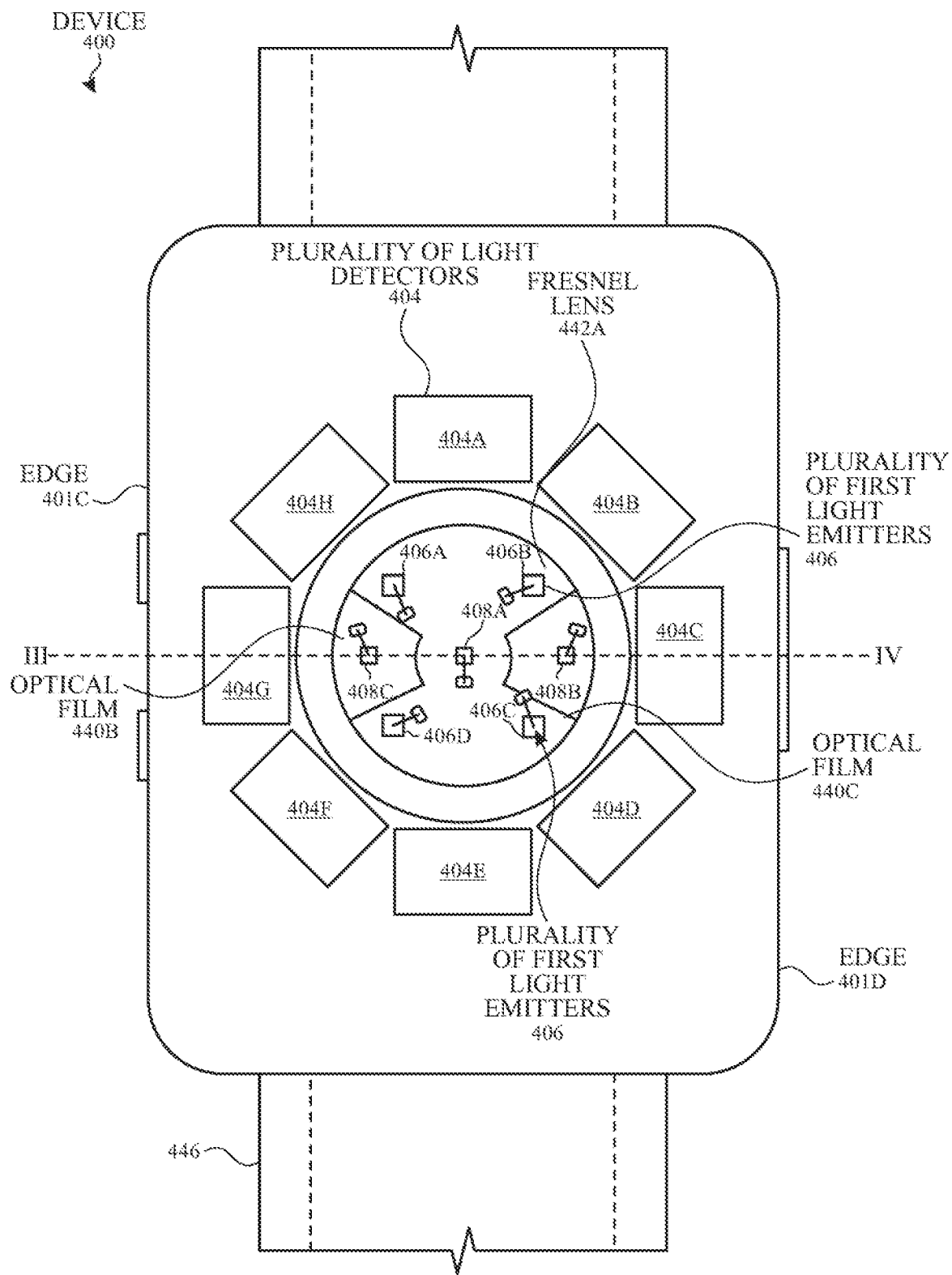
FIG. 4A illustrates a top view of an exemplary electronic device including components for generating multiple independent light beams according to examples of the disclosure.
Figure 4B:
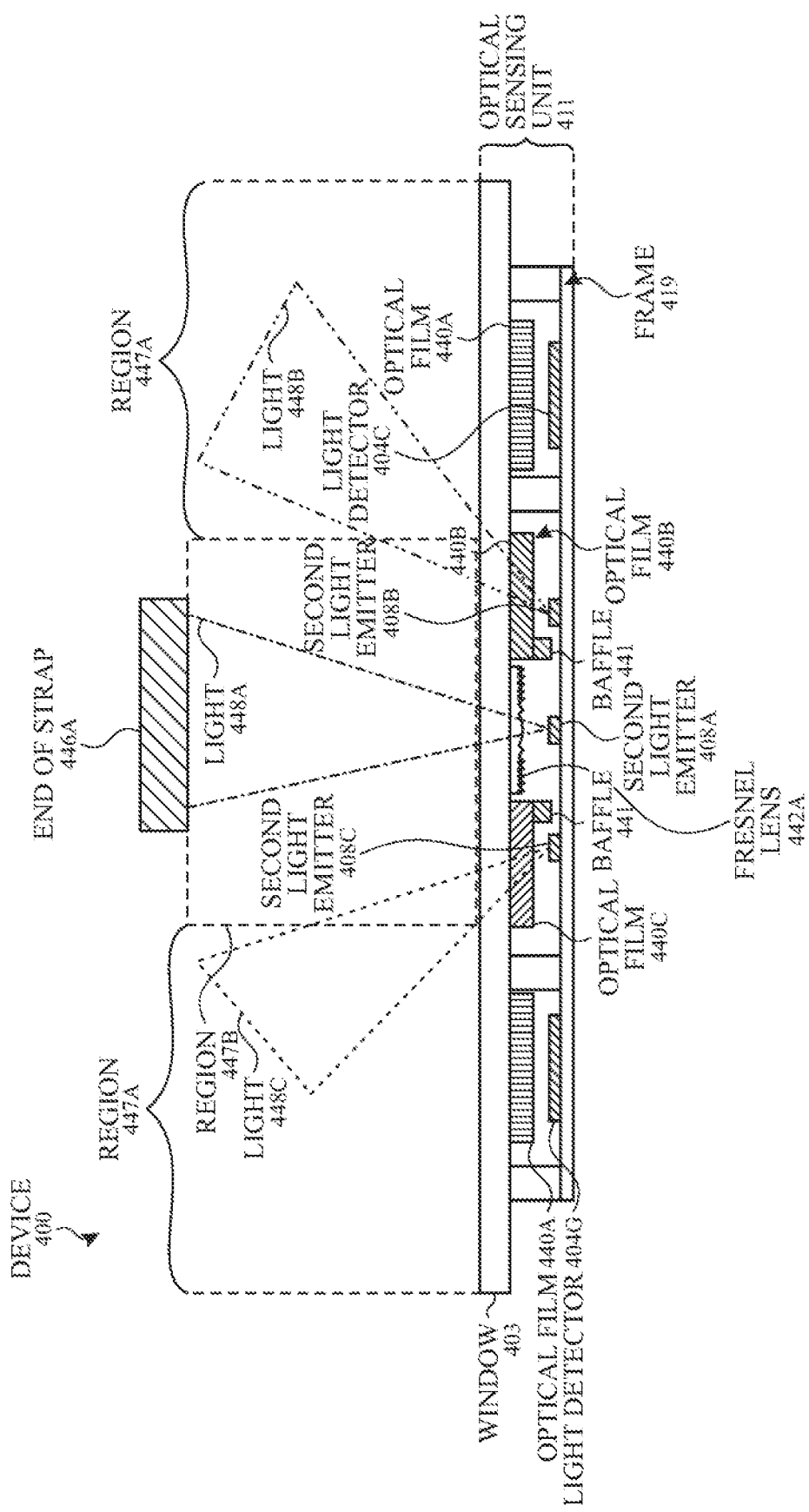
FIG. 4B illustrates a cross-sectional view of FIG. 4A along line III-IV and separated light beams according to examples of the disclosure.

In some examples, the device can include multiple light sources to distinguish between a user and an object. The multiple light sources can generate multiple independent light beams. The multiple independent light beams may allow the device the capability of determining the sub-states of the device such as whether the device is located on a surface, inside an object (e.g., a backpack), and the like. FIG. 4A illustrates a top view of an exemplary electronic device including components for generating multiple independent light beams according to examples of the disclosure. FIG. 4B illustrates a cross-sectional view of FIG. 4A along line III-IV.

Device 400 can include an optical sensing unit 411. The optical sensing unit 411 can include a plurality of light detectors 404, a plurality of first light emitters 406, and a Fresnel lens 442A, which may be correspondingly similar to the plurality of light detectors 204, the plurality of first light emitters 206, and the Fresnel lens 242A. Additionally, the device 400 may include one or more components (e.g., optical isolation) and/or may be similarly configured as device 200. The device 400 may also include a plurality of second light emitters 408, which may be correspondingly similar to the plurality of second light emitters 208.

In some examples, the device 400 can include at least three second light emitters 408A, 408B, and 408C. The second light emitters 408 can be configured to emit multiple independent light beams. For example, the second light emitter 408A can be configured to emit light 448A, the second light emitter 408B can be configured to emit light 448B, and the second light emitter 408C can be configured to emit light 448C. In this manner, the device 400 can generate multiple independent light beams using different light emitters for generating each light beam. Light beams are independent when generated by light emitters that can operate independent from other light emitters. In some instances, adjacent light beams may be separated by a gap (e.g., including air) at the location where the light beam is incident on at the end 446A of the strap, as shown in FIG. 4B.

The plurality of second light emitters 408 can be configured such that the independent light beams have one or more properties that differ. For example, at least one light beam can be a center light beam that travels through a region 447B and can be incident on the end of the strap 446A). The region 447B may be located between the strap 446 and the optical sensing unit 411. The other light beams, such as light 448B and light 448C, can at least partially travel through the region 447B, but can be directed towards regions 447A, which may be located outside of the strap 446. In this manner, light 448B and light 448C may not be incident on the strap 446.

In some examples, the second light emitter 408 can be configured such that the independent light beams have one or more properties that may be the same, such as the wavelengths. For example, some (or all) of the second light emitters 408 can emit infrared light. In some instances, the second light emitters 408 can emit infrared light, but at different wavelengths in the infrared. At least two independent light beams can be used to determine the state of the device, as discussed below.

Additionally or alternatively, the second light emitters 408 may have different operation modes. For example, the second light emitter 408A may have at least two operation modes: one for physiological measurements and another for detecting the state of the device, while the second light emitters 408B and 408C may have one operation mode for detecting the state of the device. In some instances, as discussed below, detecting the state of the device may utilize all of the second light emitters 408 or may only utilize a subset.

The device 400 may also include other optical components such as one or more optical films 440A, 440B, and 440C. The optical film(s) 440A can be optically coupled to the plurality of light detectors 404 and can be located between the plurality of light detectors 404 and the window 403. Optical films 440B and 440C can be correspondingly similar to optical films 240B and 240C and can be optically coupled to the plurality of second light emitters 408. The properties of the optical films 440B and 440C can be based on the configuration of the light beams, as discussed below.

In some examples, the device 400 can also include one or more Fresnel lenses 442 or multiple regions of a single Fresnel lens. The Fresnel lens 442A can be configured such that it overlays the second light emitter 408A. The Fresnel lens 442A may also be configured such that it overlays the plurality of first light emitters 406.

In some examples, at least two of the second light emitters 408 can be located at different depths from the window 403. The depth of a given second light emitter 408 can be based on the targeted profile of its respective light beam.

Examples of the disclosure can include additional Fresnel lenses optically coupled to the second light emitters. A Fresnel lens or a region of a Fresnel lens can have a single zone or multiple zones. FIGS. 4D-4E illustrate top and cross-sectional views of an exemplary Fresnel lens including multiple zones according to examples of the disclosure. The Fresnel lens 442B may include zone 443A, zones 443B, and zones 443C. The different zones may have features 449 with different properties, such as the number of teeth, tooth widths, zone widths, and the like. For example, as shown in the figure, the zone 443A can have narrower teeth than the zone 443B.

Examples of the disclosure can include the device having one Fresnel lens having multiple zones, such as Fresnel lens 442B, that overlays the optical film 440B, and another Fresnel lens having a single zone that overlays the optical film 440C (not shown).

Referring back to FIG. 4B, the device 400 may also include baffles 441. The baffles 441 can be a component configured to block light. For example, the baffles 441 can be used to prevent light mixing between light emitted by the second light emitters 408. The baffles 441 can include any type of opaque material, such as black silicone or foam. In some examples, the baffles 441 may be integrated (i.e., inseparable) with the Fresnel lens 442A (not shown), the optical film(s) 440B, the optical film 440C, or a combination thereof. For example, the baffles 441 may be disposed on the optical film 440B such that the optical film 440B is located between the baffle 441 and the window 403. In other examples, the baffles 441 may be located between the optical film 440B and the Fresnel lens 442 and may optionally be contacting the window 403. Yet in some instances, the baffles may be a separate component that is attached to the optical film 440B and/or Fresnel lens using, e.g., an adhesive, or a part integrated into the frame 419. The frame 419 can be a component that separates the second light emitters 408 from the light detectors 404. The baffles 441 need not extend from the optical film 440B to the frame 419, as shown in the figure, provided that the baffles 441 serve its function of blocking light.

Exemplary Configuration of the Optical Films and the Light Beams

The optical films may be configured to steer and/or shape light emitted by a corresponding light emitter. The optical films can be configured to direct light and/or reject/allow certain angles of light. The optical films can be used, alone or in conjunction with another optical component (e.g., Fresnel lens), to create a given configuration of the light beams. The optical films can include one or more features (e.g., slats, light tubes, pipes, apertures, masks, etc.) for changing the angle of light. For example, the optical films can include black and clear silicone layers. As shown throughout the figures, different optical films may have different properties, such as slats having different tilt angles. The properties of the optical films can depend on one or more factors such as the thickness of the optical film, the material of the optical film, the width of the strap, the distance between the strap and the optical film, and the like.

One example configuration of the optical films and the light beams is shown in FIG. 4B. The plurality of second light emitters 408 can generate independent light beams that are spatially separated in at least a portion of the region 447B between the optical sensing unit 411 and the end of the strap 446A. As shown in the figure, the second light emitter 408A can generate light 448A, the second light emitter 408B can generate light 448B, and the second light emitter 408C can generate light 448C. The second light emitter 408A can be optically coupled to the Fresnel lens 442A, which can direct light 448A towards the end of the strap 446A. That is, the center ray of light 448A can be 90 □ relative to the surface of the window 403.

The second light emitter 408B can be optically coupled to the optical film 440B, which can, alone or with a Fresnel lens, direct (e.g., steer) the light 448B to one side (e.g., the right side) of the strap 446 towards region 447A. The second light emitter 408B and its corresponding optical film 440B can be configured such that some (or all) of the light rays included in the light 448B are not incident on the strap 446. The optical film 440B can have one or more features (e.g., a plurality of slats) oriented in the same direction as light 448B is being directed towards. For example, the slats of the optical film 440B can be angled towards the right side. The center ray of light 448B may have a non-normal angle of incidence relative to the surface of the window 403.

The second light emitter 408C can be optically coupled to the optical film 440C, can direct (e.g., steer) light 448C to another side (e.g., the left side) of the strap 446. In some examples, the optical film 440C can have one or more features different from the optical film 440B; the plurality of slats in the optical film 440C can be oriented in the same direction as the light 448C, which may be in a different direction than the slats in the optical film 440B. The second light emitter 408C and the optical film 440C can be configured such that some (or all) of the light rays included in the light 448C are not incident on the strap 446. The center ray of light 448C may have a non-normal angle of incidence relative to the surface of the window 403.

In this manner, the spatially separated, independent light beams can allow the device to determine its state (using any of the described methods). In some examples, different light detectors can be associated with different light beams, and the processor can be configured to analyze the signals from the light detectors accordingly. In some instances, the association can be based on proximity. For example, the second light emitter 408C can be associated with the closest light detectors (e.g., light detector 404G and/or light detector 404H). The processor can be configured to associate the signals read out from these closest light detectors with the respective light beam. By creating spatially separated, independent light beams, the device may be more sensitive to tilt relative to other configurations, discussed below.

Figure 4C:
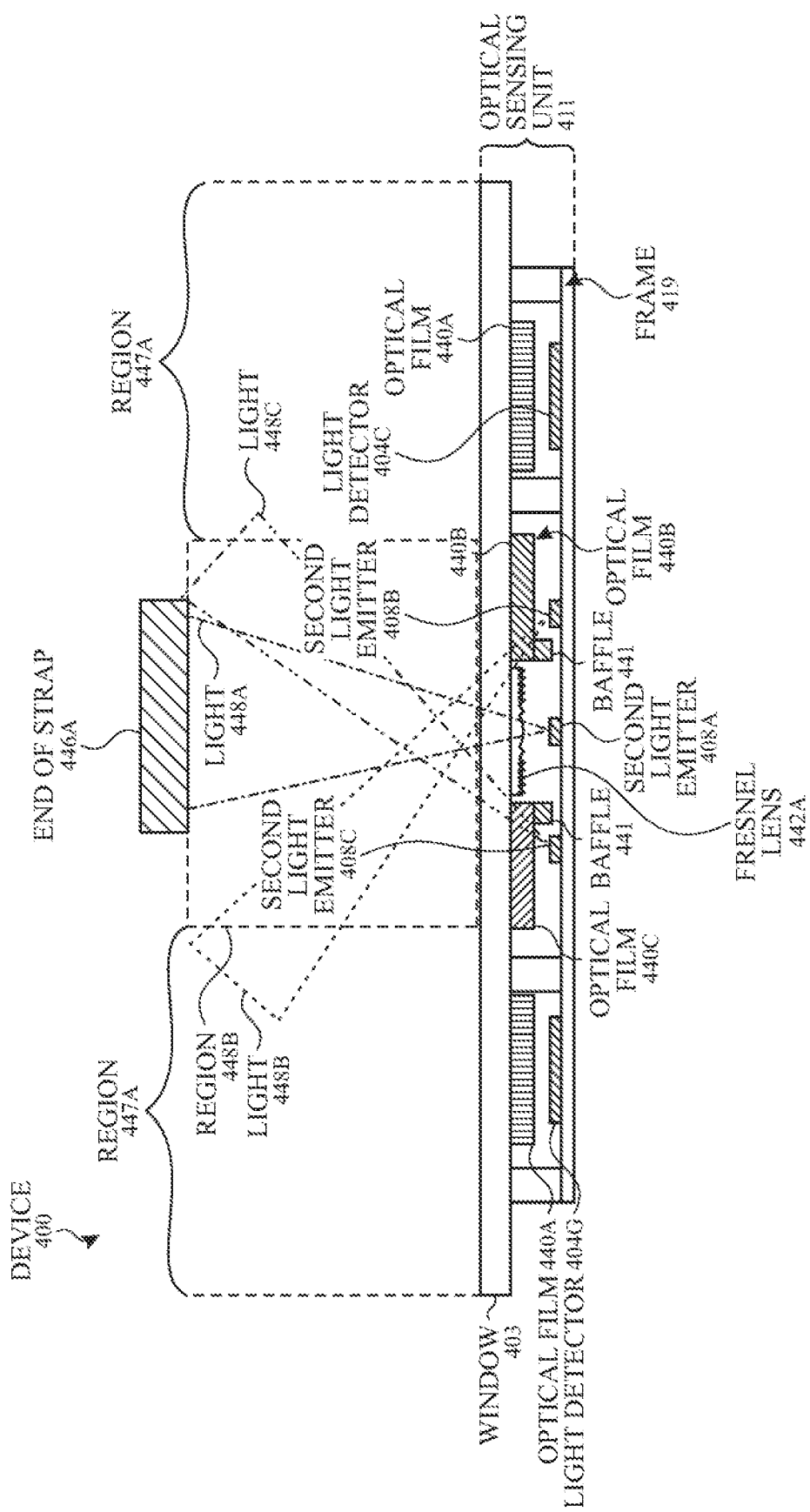
FIG. 4C illustrates a cross-sectional view of FIG. 4A along line III-IV and crossing light beams according to examples of the disclosure.

Another exemplary configuration of the optical films and the light beams is shown in FIG. 4C, where the optical film 440B can be used to direct light 448B (emitted by the light emitter 408B) towards one side (e.g., left side) of the strap 446 and the other optical film 440C can be used to direct the light 448C (emitted by the light emitter 408C) towards another side (e.g., right side) of the strap 446. Light 448B and 448C can cross over the center of the device 400. In instances where the light emitter 408B is located on the same side as the side that light 448C is directed towards and the light emitter 408C is located on the same side as the side that the light 448B is directed towards, the light 448B and 448C may intersect and cross over the center of the device 400 towards edge 401C and edge 401D shown in FIG. 4A, respectively. In some examples, the optical film(s) 440B may, alone or in conjunction with another component (e.g., Fresnel lens), direct the light 448B and 448C such that they are not, at least in entirely, incident on the strap 446.

In both of the configurations illustrated in FIGS. 4B-4C, light 448A can be a center light beam that is directed towards the strap 446 (e.g., emitted normal from the lateral surface of the window), and the light 448B and 448C can be side light beams that can be emitted at angles relative to light 448A. In the configuration of FIG. 4B, light 448B and light 448C may not intersect with light 448A. In the configuration of FIG. 4C, light 448A, light 448B, and light 448C may intersect at some point before light 448A reaches the end of the strap 446A.

Figure 5A:
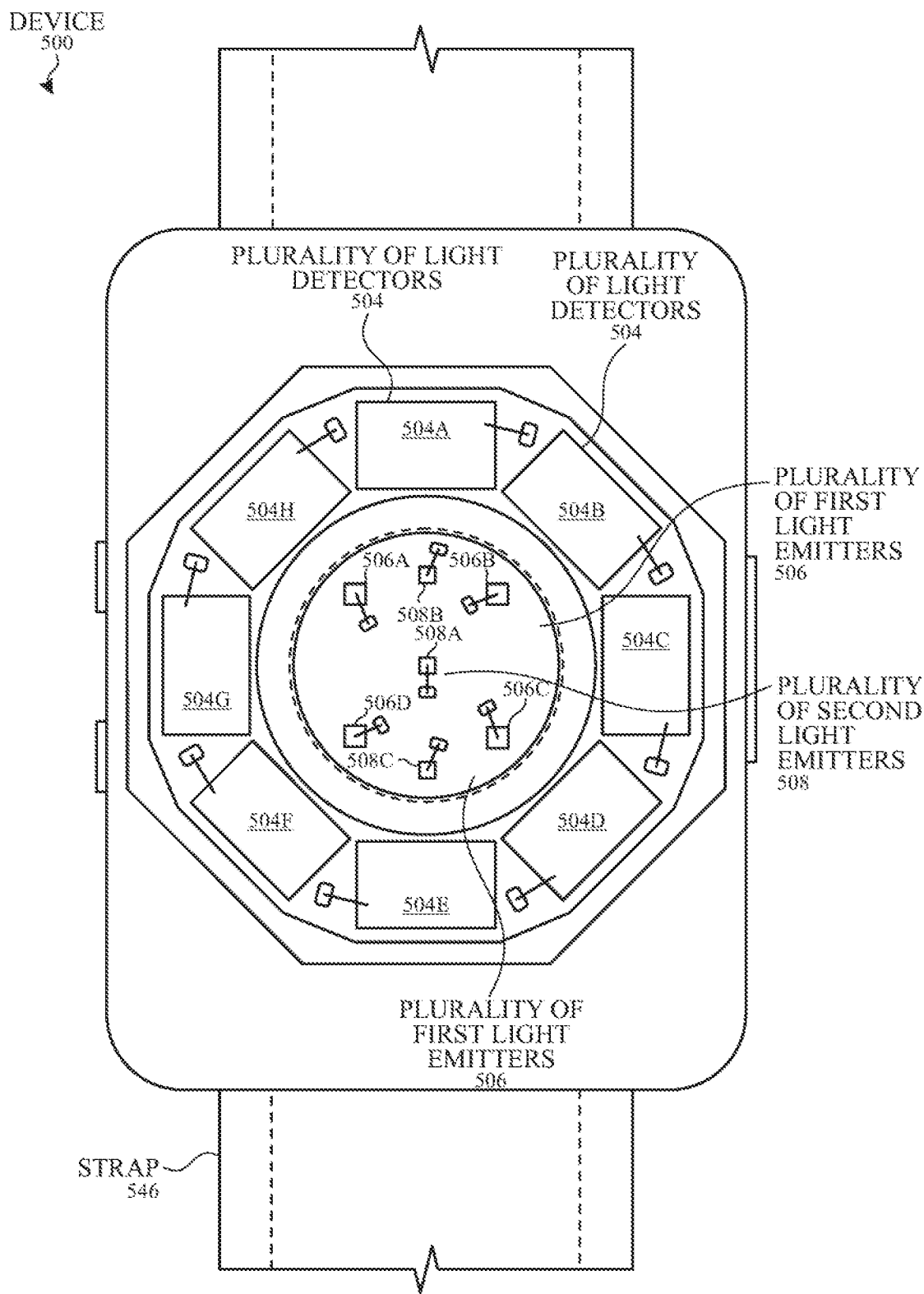
FIG. 5A illustrates a top view of an exemplary electronic device including an optical sensing unit having second light emitters located in-plane with the strap according to examples of the disclosure.

In some examples, one or more of the second light emitters can be located in other regions of the device. FIG. 5A illustrates a top view of an exemplary electronic device including an optical sensing unit having second light emitters located in-plane with the strap according to examples of the disclosure. Device 500 can include a plurality of light detectors 504, a plurality of first light emitters 506, and a strap 546, which may be correspondingly similar to the plurality of light detectors 204, the plurality of first light emitters 206, the plurality of second light emitters 408, and the strap 446. Additionally, the device 500 may include one or more components (e.g., optical isolation) and/or may be similarly configured as device 200.

At least some (e.g., two) of the plurality of second light emitters 508B and 508C can be located in-plane with the strap 546. The term "in-plane" refers to an imaginary line when drawn between the second light emitters 508B and 508C that is in the same plane as the strap 546. One or more components (e.g., optical films, Fresnel lens, etc.) of the device can be configured to steer the light from the second light emitters 508B and 508C to form one or more configurations that correspond to FIG. 4B or 4C.

Figure 5B:
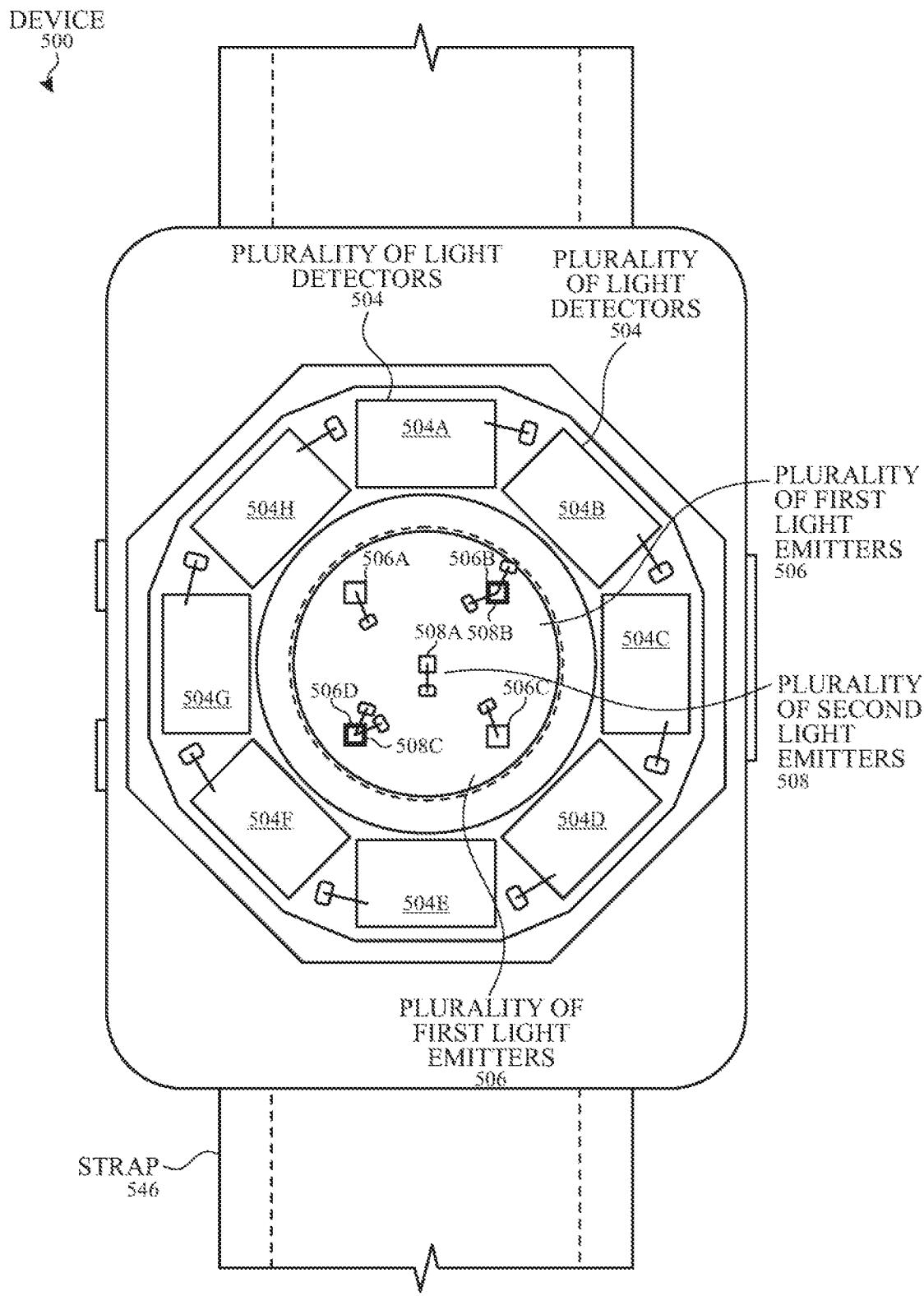
FIG. 5B illustrates a top view of an exemplary electronic device including an optical sensing unit including first and second light emitters integrated into a single emitter according to examples of the disclosure.

Examples of the disclosure may also include at least some first and second light emitters being integrated into a single light emitter, as shown in FIG. 5B. The device 500 can include light emitters configured for both physiological measurements and determining the state of the device. In some examples, a light emitter can comprise of a first light emitter 506 and a second light emitter 508, as shown in the figure, where each region can be uniquely dedicated for physiological measurements or determining the state of the device, respectively.

Examples of the disclosure also include a light emitter that has a single region configured for both physiological measurements and determining the state of the device. Information for the different types of measurements can be extracted based on, e.g., wavelength selection, where a first set of wavelengths of the measured return light can be used for the physiological measurements, and a second set of wavelengths can be used for determining the state of the device.

Exemplary Device Operation for Multiple Independent Light Beams

As discussed above, the device can be configured to use multiple independent light beams to determine the state of the device using one or more operation modes. Some devices may be limited to using only one operation mode based on, e.g., programmed settings. Other devices may switch between different operation modes depending on one or more factors such as the power level of the device, the amount of motion associated with the device, the location of the device, the amount of noise in the signals, and the like.

Figure 6A:
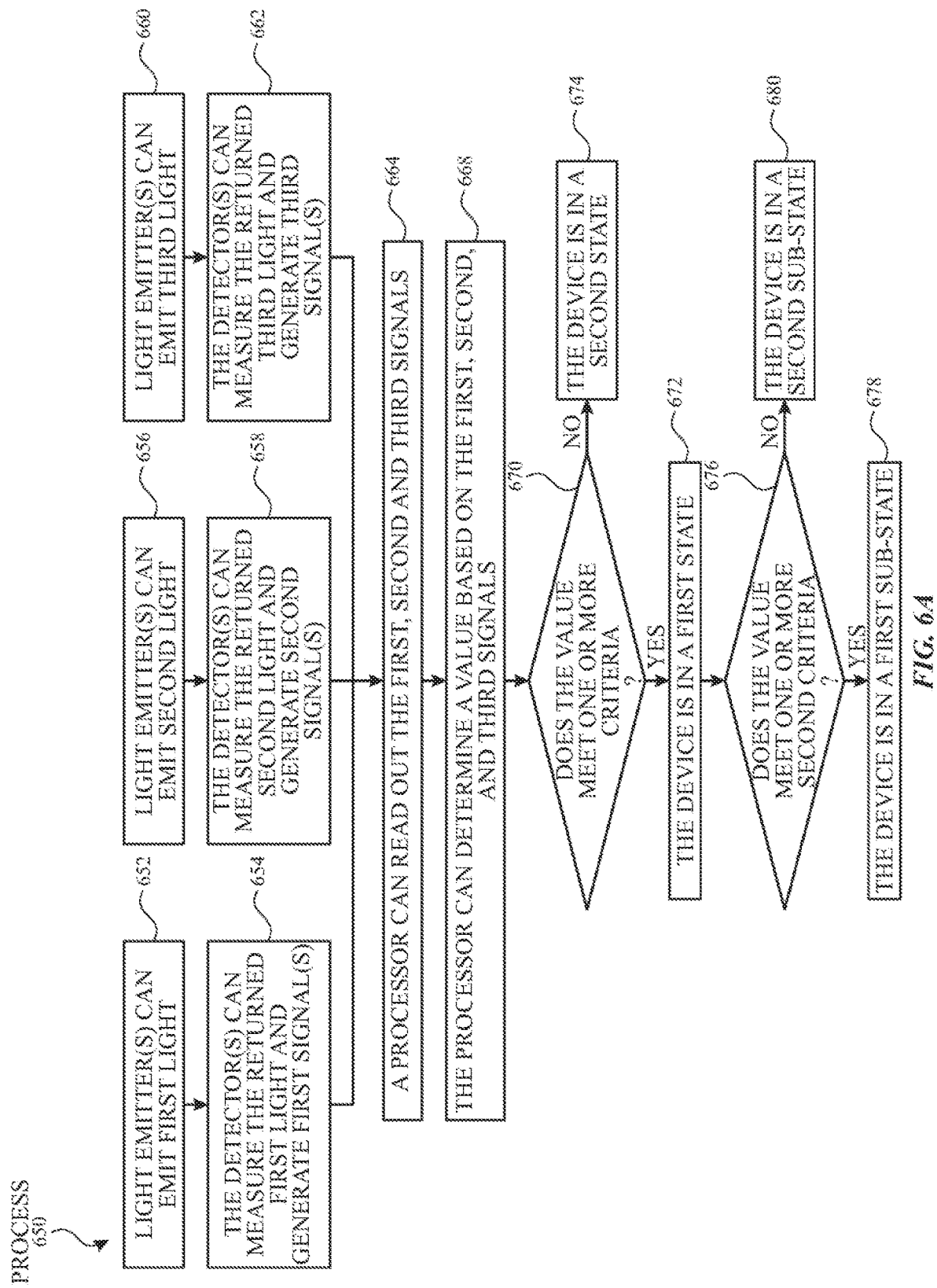
FIG. 6A illustrates an exemplary process flow for operating the optical sensing unit to determine a state of the device using all of the independent light beams according to examples of the disclosure.

In one operation mode, the device can emit all (e.g., three) independent light beams for determining the state of the device. FIG. 6A illustrates an exemplary process flow for operating the optical sensing unit to determine the state of the device using all of the independent light beams according to examples of the disclosure. One or more light emitters (e.g., second light emitter 408A illustrated in FIG. 4B) can emit first light (e.g., infrared light 448A illustrated in FIG. 4B) (step 652 of process 650). One or more detectors can measure the returned first light and generate one or more first signals indicative of the measured returned first light (step 654 of process 650). Similarly, one or more light emitters (e.g., second light emitter 408B illustrated in FIG. 4B) can emit second light (e.g., infrared light 448B illustrated in FIG. 4B) (step 656 of process 650). One or more detectors can measure the returned second light and generate one or more second signals indicative of the measured returned second light (step 658 of process 650). One or more light emitters (e.g., second light 408C illustrated in FIG. 4B) can emit third light (e.g., infrared light 448C illustrated in FIG. 4B) (step 660 of process 650). One or more detectors can measure the returned third light and generate one or more third signals indicative of the measured returned third light (step 662 of process 650).

Examples of the disclosure can include emitting all of the light beams in steps 652, 656, and 660 at the same time, and measuring the corresponding return light at steps 654, 658, and 662 at the same time. Alternatively, at least two of the light beams can be emitted at different times. For example, the first light can be the center light beam that is emitted and measured first. The second and third light can be side light beams that are emitted and measured after. The frequency of the emission of the first light and measurement of its corresponding return light may differ (e.g., be more frequent) than the frequency of the emission of the second and third light and measurement of its corresponding return light, for example. In some instances, the second and third signals (corresponding to the returned second and returned third light) may be tied together and read out as a single signal, in some examples.

A processor can read out the first, second, and third signals (step 664 of process 650). The processor can determine one or more values using the first, second, and third signals (step 668 of process 650). For example, the processor can sum the second and third signals and divide the sum(s) by the first signal(s) to lead to a value. The processor can determine whether the value meets one or more criteria (step 670 of process 650). If the value meets the criteria, then the processor can determine that the device is in a first state (step 672 of process 650). If the value does meet the criteria, then the processor can determine that the device is in a second state (step 674 of process 650).

In some examples, one or more states of the device can involve sub-states, and the device can be configured for determining the sub-state of the device. For example, the first state can be an off-wrist state, which can include a plurality of sub-states such as the device is on the user's fingers, the device resting on a table, the device is in a bag/backpack, or the like. In some instances, the processor can determine the sub-state of the device using the value determined in step 668. For example, the device can have one or more second criteria that may be related to the expected reflectance values of skin. A determined value that meets both the first and the second criteria can correlate to device 600 having a state of being off-wrist and a sub-state of the strap 646 of the device resting on the user's fingers 690, as shown in FIG. 6B.

Alternatively, the device can determine the sub-state based on multiple determined values: the first value can meet the first criteria, and the second value can meet the second criteria. The first and second values may include different signals. For example, the first value may be determined using the first, second, and third signals, such as taking the first signal and dividing by the sum of the second and third signals. The second value may be determined using the first and second signals, such as taking the ratio of the first signal to the second signal. Alternatively, the second value can be determined using the first and third signals, such as taking the ratio of the first signal to the third signal. As another option, the second value can be determined using the second and third signals. As yet another option, the sub-state can be determined based on a determined value and one or more signals themselves (e.g., the second signal is indicative of the expected reflectance of skin).

Figure 6B:
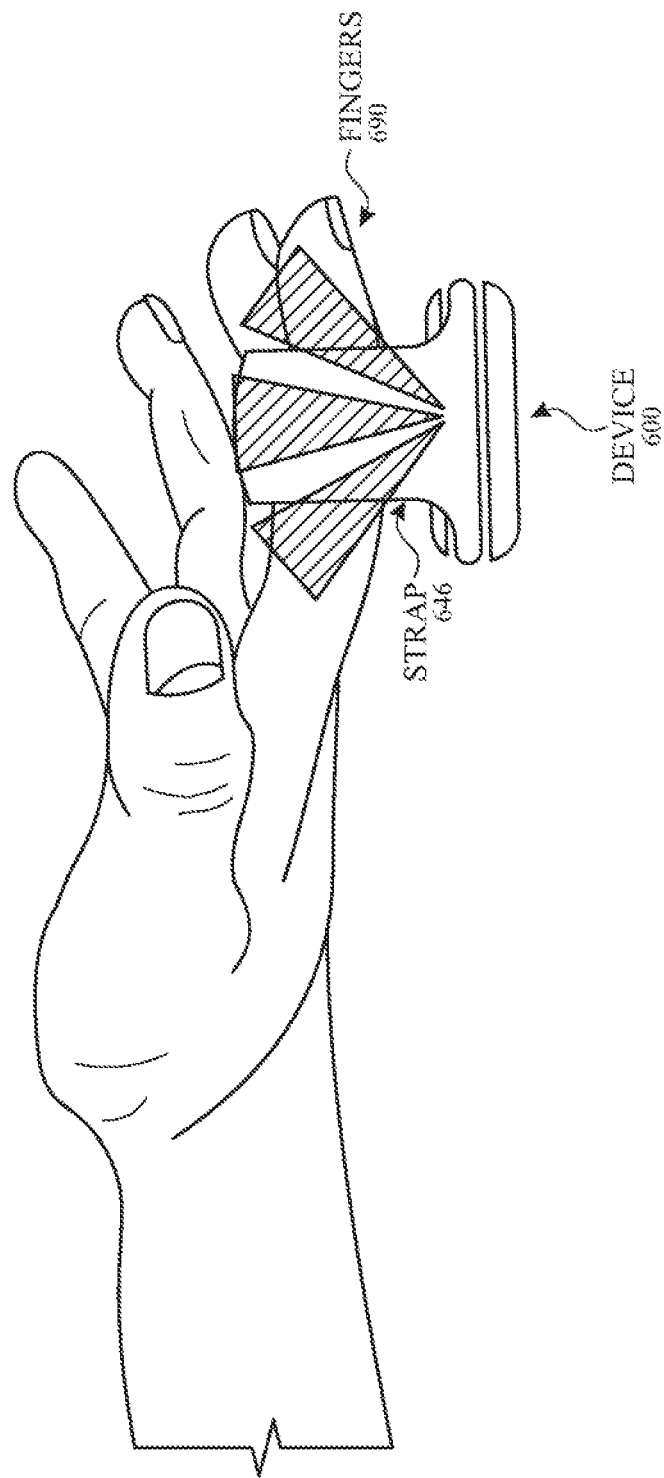
FIG. 6B illustrates a device having an exemplary state of being off-wrist state and sub-state of the device being resting on the user's fingers according to examples of the disclosure.
Figure 7A:
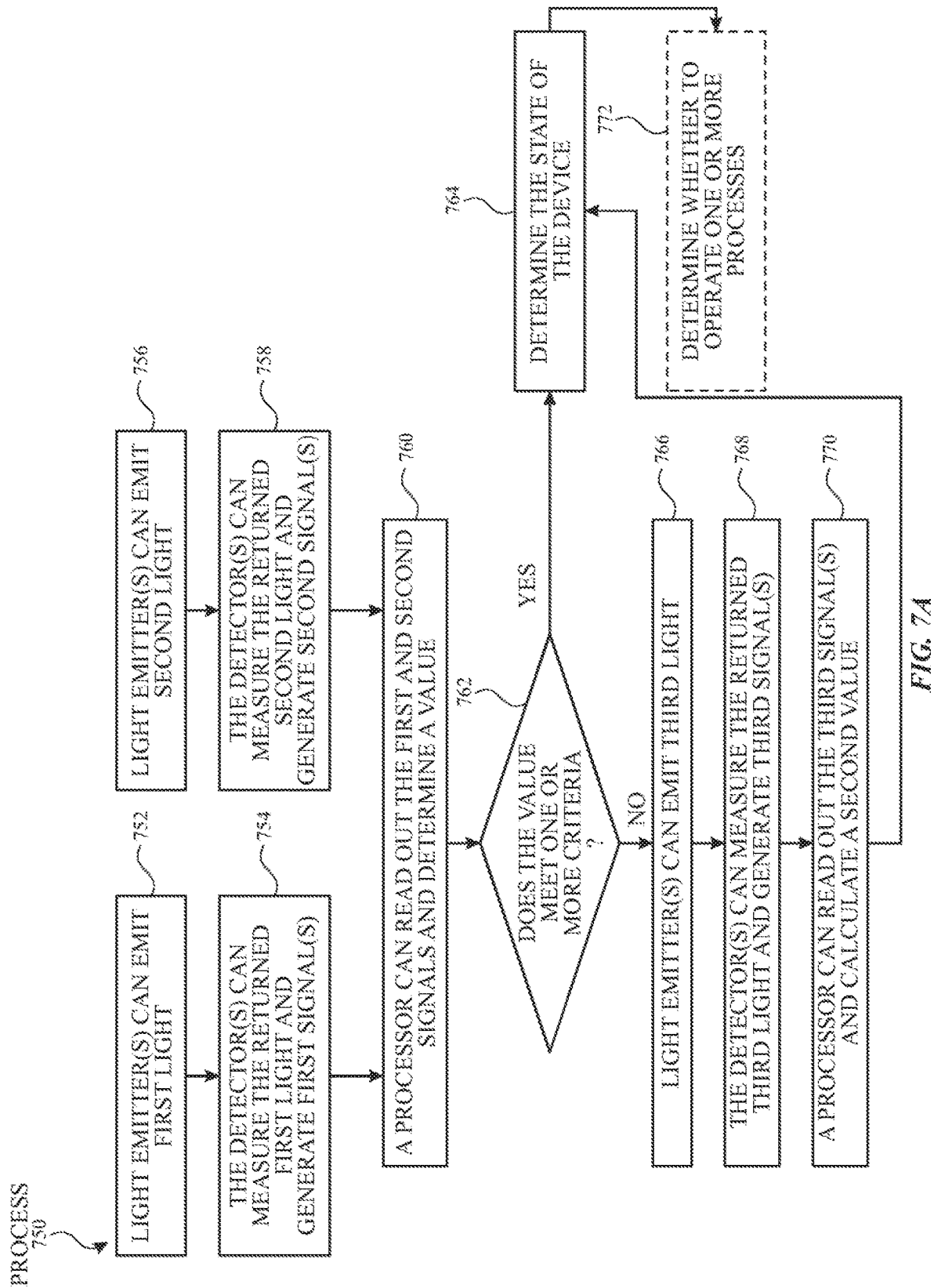
FIG. 7A illustrates an exemplary process flow for activating the light beams of an optical sensing unit based on measurement information according to examples of the disclosure.
Figure 8:
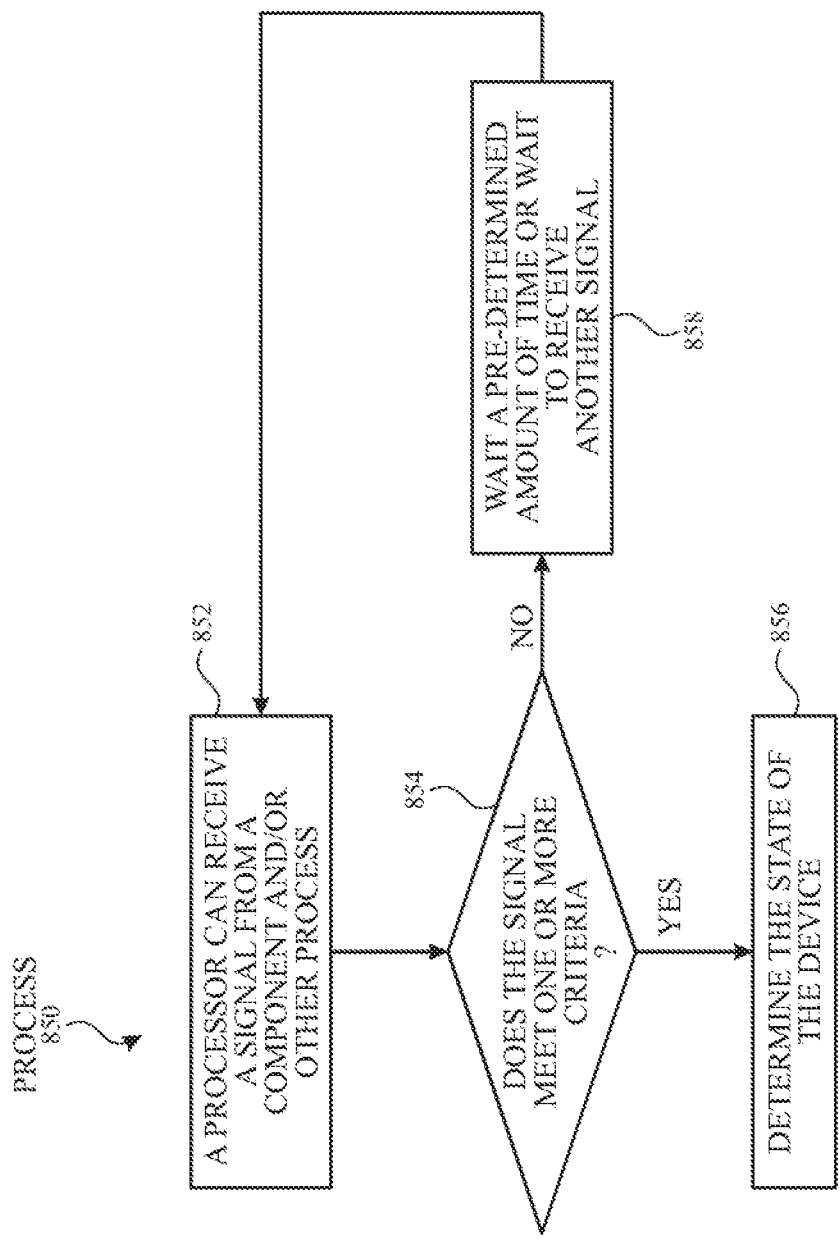
FIG. 8 illustrates an exemplary process flow for activating the light beams of an optical sensing unit based on information from other components and/or processes according to examples of the disclosure.

Although FIG. 6B illustrates an exemplary state and sub-state of the device that can be detected using the operation illustrated in FIG. 6A, examples of the disclosure can include using other operations such as those illustrated in FIGS. 3C, 7A, and 8 to detect the device being on the user's fingers.

In another operation mode, the device can emit less than all (e.g., two) of the independent light beams and can dynamically (i.e., in real-time) determine whether to activate the remaining light beams based on measurement information. FIG. 7A illustrates an exemplary process flow for activating the light beams of an optical sensing unit based on measurement information according to examples of the disclosure. One or more light emitters (e.g., second light emitter 408A illustrated in FIG. 4B) can emit a first light (e.g., light 448A illustrated in FIG. 4B) (step 752 of process 750). At a least portion of it can return back to the device as returned first light, and one or more light detectors (e.g., the plurality of light detectors 404 illustrated in FIG. 4A) can generate one or more first signals indicative of the returned first light (step 754 of process 750). The first signal can be indicative of the properties of the returned first light.

One or more light emitters (e.g., second light emitter 408B illustrated in FIG. 4B) can emit a second light (e.g., light 448B illustrated in FIG. 4B) (step 756 of process 750). At least a portion of it can return back to the device as returned second light, and one or more light detectors can generate one or more second signals indicative of the properties of the returned second light (step 758 of process 750). In some examples, the device may include other second light emitters (e.g., second light emitter 408C illustrated in FIG. 4B), which may not be active (e.g., on) at the time of step 752A, step 752B, or both.

A processor can read out the first and second signals and can process them separately or together to determine at least one first value (step 760 of process 750). In some examples, the at least one first value can be a figure of merit. The processor can check if the first value meets one or more criteria (e.g., exceeds a pre-determined threshold value) (step 762 of process 750). If the first value meets the criteria, then it can be used to determine the state of the device (step 764 of process 750).

Exemplary criteria include, but are not limited to, the confidence level meeting a certain threshold value, the signal-to-noise ratio meeting a certain threshold value, the motion sensors indicating the motion state of the device matches a pre-determined motion, the position sensors indicating the position of the device matches a pre-determined position, and the battery level meeting a certain threshold value.

The first value can be determined as equal to the first signal, the second signal, the sum of the first and second signals, the ratio of the first signal to second signal, the ratio of the second signal to the first signal, or the difference between the first and second signal.

If the criteria is not met, one or more light emitters (e.g., second light emitter 708C illustrated in FIG. 7B) can emit a third light (e.g., light 748C illustrated in FIG. 7B) (step 766 of process 750). At a least portion of it can return back to the device as returned first light, and one or more light detectors (e.g., the plurality of light detectors 404 illustrated in FIG. 4A) can generate one or more first signals indicative of the returned first light (step 768 of process 750). The third signal can be indicative of the properties of the returned third light.

A processor can receive the third signal can be process it separately or together with the first and/or second signals to determine at least one second value (step 770 of process 750). In some examples, the first value determined at step 760 may differ from the second value determined at step 768. In some instances, the first and second values at the two steps may be determined using different methods (e.g., algorithms). The second value can be used to determine the state of the device (in step 764).

Figure 7B:
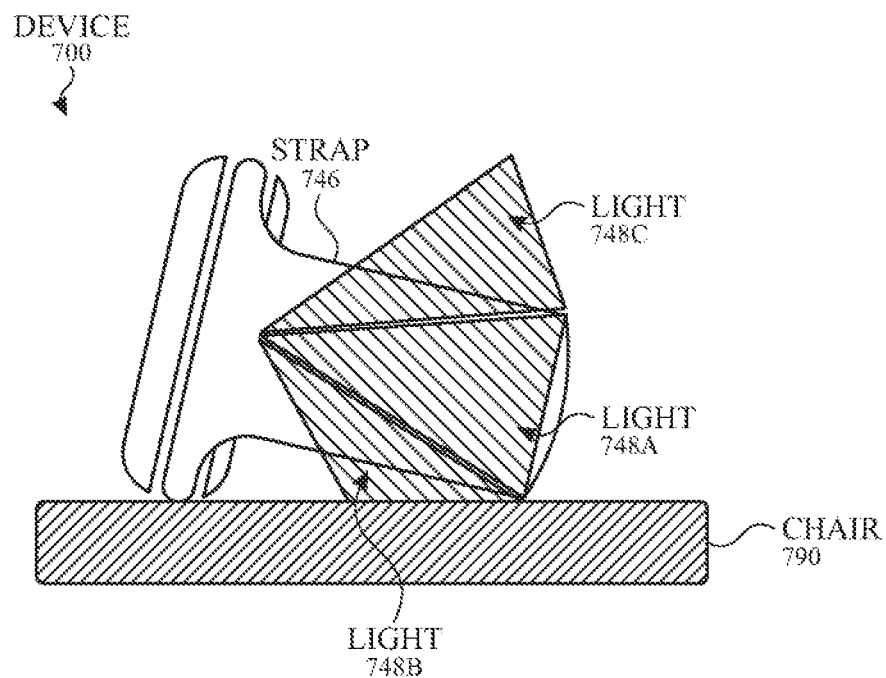
FIG. 7B illustrates an exemplary device having an off-wrist state and a resting on a chair with its crown up sub-state according to examples of the disclosure.

Although not illustrated in the figure, examples of the disclosure can include calculating a first value in step 760 and calculating a second value in step 768, where at least one signal in step 760 may differ from those signals used in the calculation of step 768. FIG. 7B illustrates an exemplary device having an off-wrist state and a resting on a chair with its crown up sub-state according to examples of the disclosure. The device 700 may emit the light 748A and light 748B. The device 700 may receive first and second signals indicative of portions that have returned from light 748A and light 748B, respectively. Light 748A may be incident on the strap 746, and its corresponding first signal may be indicative of such. Light 748B may be incident on a chair 790, and its corresponding second signal may be indicative of such. The device may, at step 760, determine the ratio of the first signal to the second signal, for example. Since light 748B is incident on the chair 790, the value determined may meet the criteria (determined at step 762). At step 764, the processor may determine that the device is off-wrist.

Alternatively, the criteria at step 762 may be a confidence level of the value being above a threshold confidence level. The first value may indicate that the light beam is incident on an object, but the value may correspond to an object having a fabric-like material. The fabric-like material may be the user's shirt, which may lead to a lower confidence level as the device 700 may nevertheless be on-wrist. The process may then proceed onto steps 766 and 768 to gather more information for determining the state of the device. The device 700 may emit light 748C, and the third signal may indicate the return of light 748C. If the third signal corresponds to a low return value, the processor may determine at step 764 that the device is off-wrist. As another example, if the third signal corresponds to light returning from skin, the processor may determine that the device is on-wrist. Yet in another example, if the third signal corresponds to light returning from an object having a fabric-like material, the processor may determine that the device is off-wrist and has a sub-state of being in a backpack, purse, or bag.

As another example, the characteristics of the device may trigger one or more processes, such as whether to disable the display and touch sensing capabilities when the device is face down (as any registered touches will likely be false touches). The device 700 may emit light 748A and light 748C. Light 748C may not be incident on an object (or may be incident on an object too remote for the light to return), so the processor may determine that the device is off-wrist. In some examples, step 762 may be skipped once the device is determined to be off-wrist.

Figure 7C:
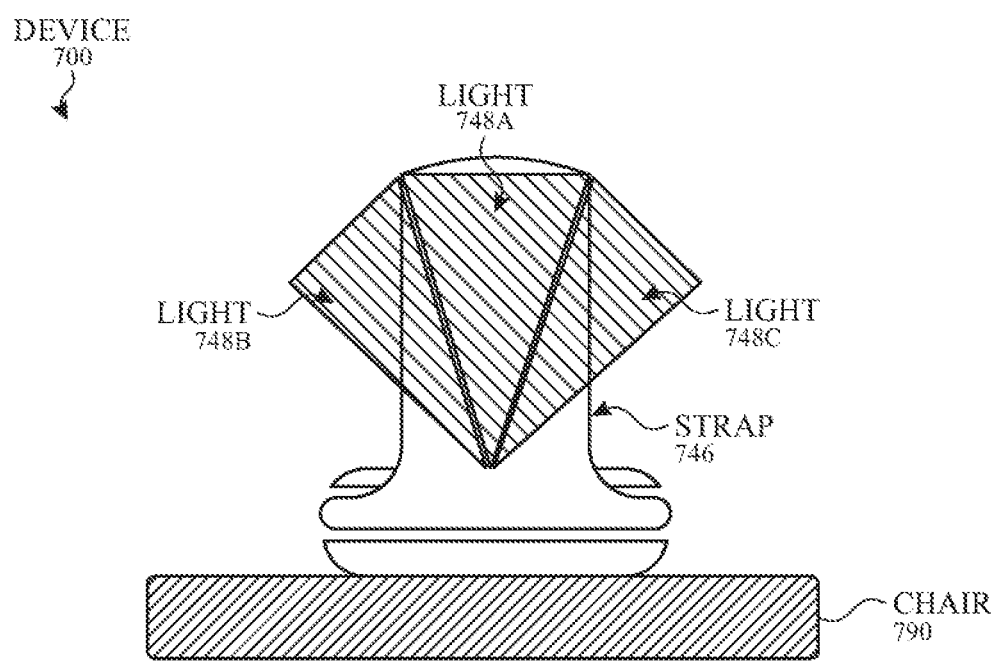
FIG. 7C illustrates an exemplary state of the device, which may be off-wrist and resting on a chair with its face down, according to examples of the disclosure.

The process may proceed with steps 766 and 768 to determine the sub-state of the device: whether the device is face down (as shown in FIG. 7C) or not (as shown in FIG. 7B). In step 766, the device can use a second light emitter to emit light 748B. If the signal associated with the returned portion of light 748B indicates that light 748B is not incident on an object, then the processor may be determine that the device is off-wrist and face down, so it can determine whether to operate one or more processes (step 772 of process 750) such as disabling the display and touch sensing capabilities.

In yet another example, the value determined at step 760 may involve the differences between the magnitudes of the first and second signals. The differences may not be enough to be indicative of the state of the device. The second light emitter(s) can emit third light in step 766, and the second value in step 770 can be indicative of the differences among the first, second, and third signals. If the first, second, and third signals have magnitudes that vary in accordance with respective locations of the corresponding second light emitters on the device, the processor may determine at step 764 that the device is on-wrist. The variation in magnitudes of the first, second, and third signals may be due to the device being tilted while being worn. In some examples, the processor may be able to distinguish between the device being tilted and worn on the user and the device being tilted and resting on surface (such as shown in FIG. 7B) based on whether the returned first, second, and/or light corresponding to skin.

One or more steps as illustrated in FIG. 7A and any of the figures related to a process can be implemented in an order different than what is shown in the figures. As one example, steps 756 and 758 can follow step 762, where the use of the second light can be based on the determination of whether the value meets one or more criteria (at step 762).

Device can have multiple operation modes, such as one where the device can use information from other components included in the device and/or from other processes to determine whether to activate the remaining light beams. FIG. 8 illustrates an exemplary process flow for activating the light beams of an optical sensing unit based on information from other components and/or processes according to examples of the disclosure. The processor can receive a signal from a component (e.g., not included in the optical sensing unit) and/or other process (step 852 of process 850). The processor can determine whether the signal meets one or more criteria (step 854 of process 850). If the criteria is met, the processor can execute a process for determining the state of the device (step 856 of process 850), such as process 650 of FIG. 6A or process 750 of FIG. 7A. If the criteria has not been met, the processor can wait a certain amount of time (step 858 of process 850) or can wait to receive another signal from the same or another component or process before subsequently determining again if the criteria is met, using the same signal or another signal (in step 854).

Exemplary signals that the processor can receive and associated components can include a valid password input from a touch screen, the current power level from a battery manager, a motion signal from an accelerometer, a proximity determination using information from a physiological measurement, and the like.

For example, the center light beam (e.g., light 748A illustrated in FIGS. 7B-7C) can be used for proximity determination. The processor can receive this signal indicative of the proximity determination from another process. If the processor determines that the device is not proximate to the user's wrist, then the process can proceed to step 856. In this manner, the device can activate the center second light emitter more frequently as an initial rough determination as to whether the device is off-wrist, and then may activate the other second light emitters (at the cost of consuming power) to make a more accurate determination.

As another example, the processor can receive a motion signal from the accelerometer. If the device is moving, then the device is likely on the user's wrist, where the processor can wait until the device stops moving before making the determination of whether the device is off-wrist.

Overview of the Computing System and Host Devices

Figure 9:
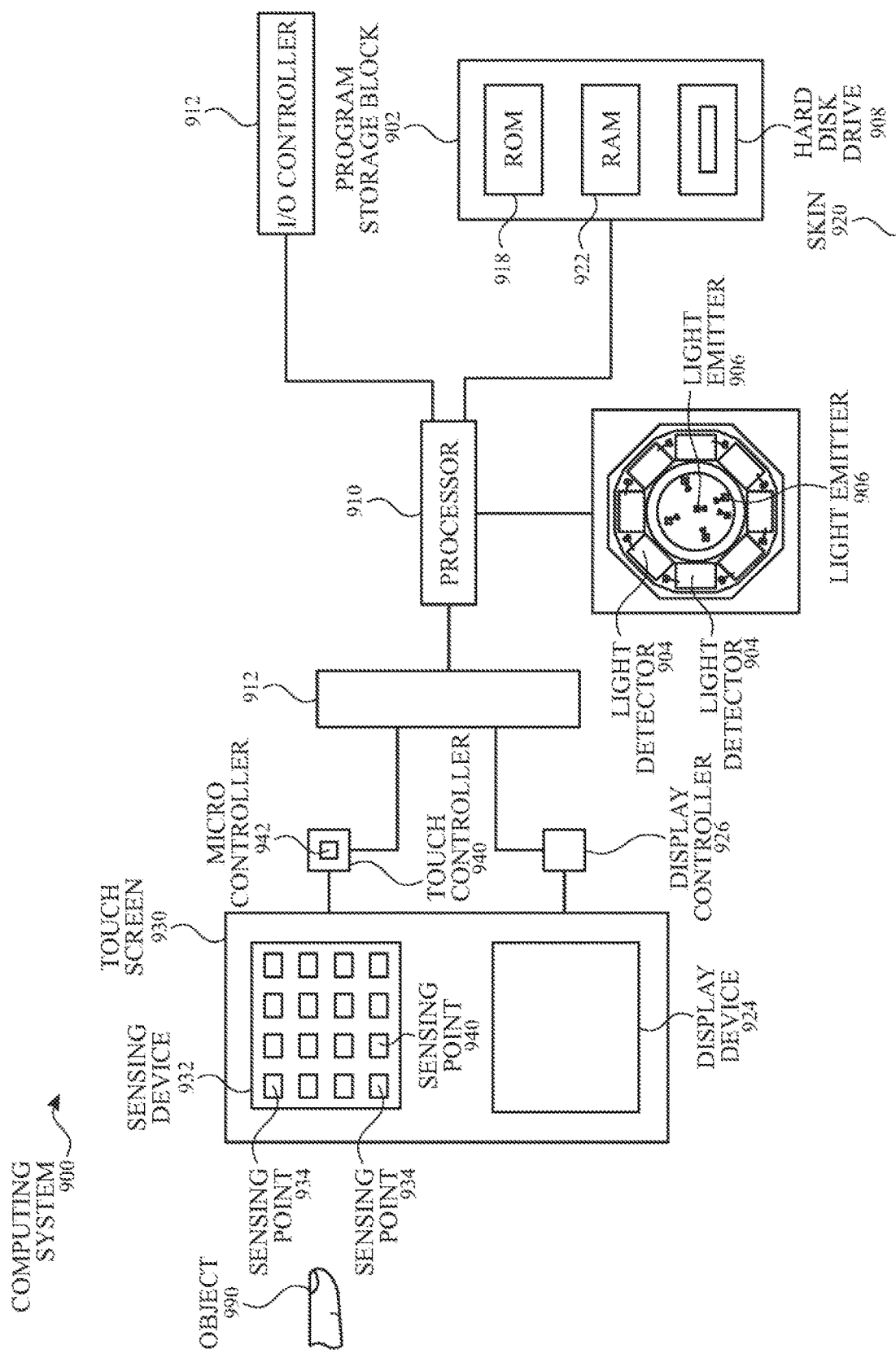
FIG. 9 illustrates an exemplary block diagram of a computing system comprising an optical sensing unit according to examples of the disclosure.

FIG. 9 illustrates an exemplary block diagram of a computing system comprising the concentric architecture for optical sensing according to examples of the disclosure. Computing system 900 can correspond to any of the computing devices illustrated in FIGS. 1A-1C. Computing system 900 can include a processor 910 configured to execute instructions and to carry out operations associated with computing system 900. For example, using instructions retrieved from memory, processor 910 can control the reception and manipulation of input and output data between components of computing system 900. Processor 910 can be a single-chip processor or can be implemented with multiple components.

In some examples, processor 910 together with an operating system can operate to execute computer code and produce and use data. The computer code and data can reside within a program storage block 902 that can be operatively coupled to processor 910. Program storage block 902 can generally provide a place to hold data that is being used by computing system 900. Program storage block 902 can be any non-transitory computer-readable storage medium (excluding signals), and can store, for example, history and/or pattern data relating to PPG signal and perfusion index values measured by one or more light detectors such as light detectors 904. By way of example, program storage block 902 can include Read-Only Memory (ROM) 918, Random-Access Memory (RAM) 922, hard disk drive 908 and/or the like. The computer code and data could also reside on a removable storage medium and loaded or installed onto the computing system 900 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 900 can also include an input/output (I/O) controller 912 that can be operatively coupled to processor 910, or it can be a separate component as shown. I/O controller 912 can be configured to control interactions with one or more I/O devices. I/O controller 912 can operate by exchanging data between processor 910 and the I/O devices that desire to communicate with processor 910. The I/O devices and I/O controller 912 can communicate through a data link. The data link can be a one-way link or a two-way link. In some cases, I/O devices can be connected to I/O controller 912 through wireless connections. By way of example, a data link can correspond to PS/2, USB, Firewire, IR, RF, Bluetooth or the like.

Computing system 900 can include a display device 924 that can be operatively coupled to processor 910. Display device 924 can be a separate component (peripheral device)

or can be integrated with processor 910 and program storage block 902 to form a desktop computer (e.g., all-in-one machine), a laptop, handheld or tablet computing device of the like. Display device 924 can be configured to display a graphical user interface (GUI) including perhaps a pointer or cursor as well as other information to the user. By way of example, display device 924 can be any type of display including a liquid crystal display (LCD), an electroluminescent display (ELD), a field emission display (FED), a light emitting diode display (LED), an organic light emitting diode display (OLED) or the like.

Display device 924 can be coupled to display controller 926 that can be coupled to processor 910. Processor 910 can send raw data to display controller 926, and display controller 926 can send signals to display device 924. Data can include voltage levels for a plurality of pixels in display device 924 to project an image. In some examples, processor 910 can be configured to process the raw data.

Computing system 900 can also include a touch screen 930 that can be operatively coupled to processor 910. Touch screen 930 can be a combination of sensing device 932 and display device 924, where the sensing device 932 can be a transparent panel that is positioned in front of display device 924 or integrated with display device 924. In some cases, touch screen 930 can recognize touches and the position and magnitude of touches on its surface. Touch screen 930 can report the touches to processor 910, and processor 910 can interpret the touches in accordance with its programming. For example, processor 910 can perform tap and event gesture parsing and can initiate a wake of the device or powering on one or more components in accordance with a particular touch.

Touch screen 930 can be coupled to a touch controller 940 that can acquire data from touch screen 930 and can supply the acquired data to processor 910. In some cases, touch controller 940 can be configured to send raw data to processor 910, and processor 910 can process the raw data. For example, processor 910 can receive data from touch controller 940 and can determine how to interpret the data. The data can include the coordinates of a touch as well as pressure exerted. In some examples, touch controller 940 can be configured to process raw data itself. That is, touch controller 940 can read signals from sensing points 934 located on sensing device 932 and can turn the signals into data that the processor 910 can understand.

Touch controller 940 can include one or more microcontrollers such as microcontroller 942, each of which can monitor one or more sensing points 934. Microcontroller 942 can, for example, correspond to an application specific integrated circuit (ASIC), which works with firmware to monitor the signals from sensing device 932, process the monitored signals, and report this information to processor 910.

One or both display controller 926 and touch controller 940 can perform filtering and/or conversion processes. Filtering processes can be implemented to reduce a busy data stream to prevent processor 910 from being overloaded with redundant or non-essential data. The conversion processes can be implemented to adjust the raw data before sending or reporting them to processor 910.

In some examples, sensing device 932 can be based on capacitance. When two electrically conductive members come close to one another without actually touching, their electric fields can interact to form a capacitance. The first electrically conductive member can be one or more of the sensing points 934, and the second electrically conductive member can be an object 990 such as a finger. As object 990 approaches the surface of touch screen 930, a capacitance can form between object 990 and one or more sensing points 934 in close proximity to object 990. By detecting changes in capacitance at each of the sensing points 934 and noting the position of sensing points 934, touch controller 940 can recognize multiple objects, and determine the location, pressure, direction, speed, and acceleration of object 990 as it moves across the touch screen 930. For example, touch controller 940 can determine whether the sensed touch is a finger, tap, or an object covering the surface.

Sensing device 932 can be based on self-capacitance or mutual capacitance. In self-capacitance, each of the sensing points 934 can be provided by an individually charged electrode. As object 990 approaches the surface of the touch screen 930, the object can capacitively couple to those electrodes in close proximity to object 990, thereby stealing charge away from the electrodes. The amount of charge in each of the electrodes can be measured by the touch controller 940 to determine the position of one or more objects when they touch or hover over the touch screen 930. In mutual capacitance, sensing device 932 can include a two layer grid of spatially separated lines or wires (not shown), although other configurations are possible. The upper layer can include lines in rows, while the lower layer can include lines in columns (e.g., orthogonal). Sensing points 934 can be provided at the intersections of the rows and columns. During operation, the rows can be charged, and the charge can capacitively couple from the rows to the columns. As object 990 approaches the surface of the touch screen 930, object 990 can capacitively couple to the rows in close proximity to object 990, thereby reducing the charge coupling between the rows and columns. The amount of charge in each of the columns can be measured by touch controller 940 to determine the position of multiple objects when they touch the touch screen 930.

Computing system 900 can also include one or more light emitters such as light emitters 906 and one or more light detectors such as light detectors 904 proximate to skin 920 of a user. Light emitters 906 can be configured to generate light, and light detectors 904 can be configured to measure the return. Light detectors 904 can send measured raw data to processor 910, and processor 910 can determine the state of the device. Processor 910 can dynamically activate light emitters and/or light detectors based on an application, user skin type, and usage conditions. In some examples, some light emitters and/or light detectors can be activated, while other light emitters and/or light detectors can be deactivated to conserve power, for example. In some examples, processor 910 can store the raw data and/or processed information in a ROM 918 or RAM 922 for historical tracking or for future diagnostic purposes.

Figure 10:
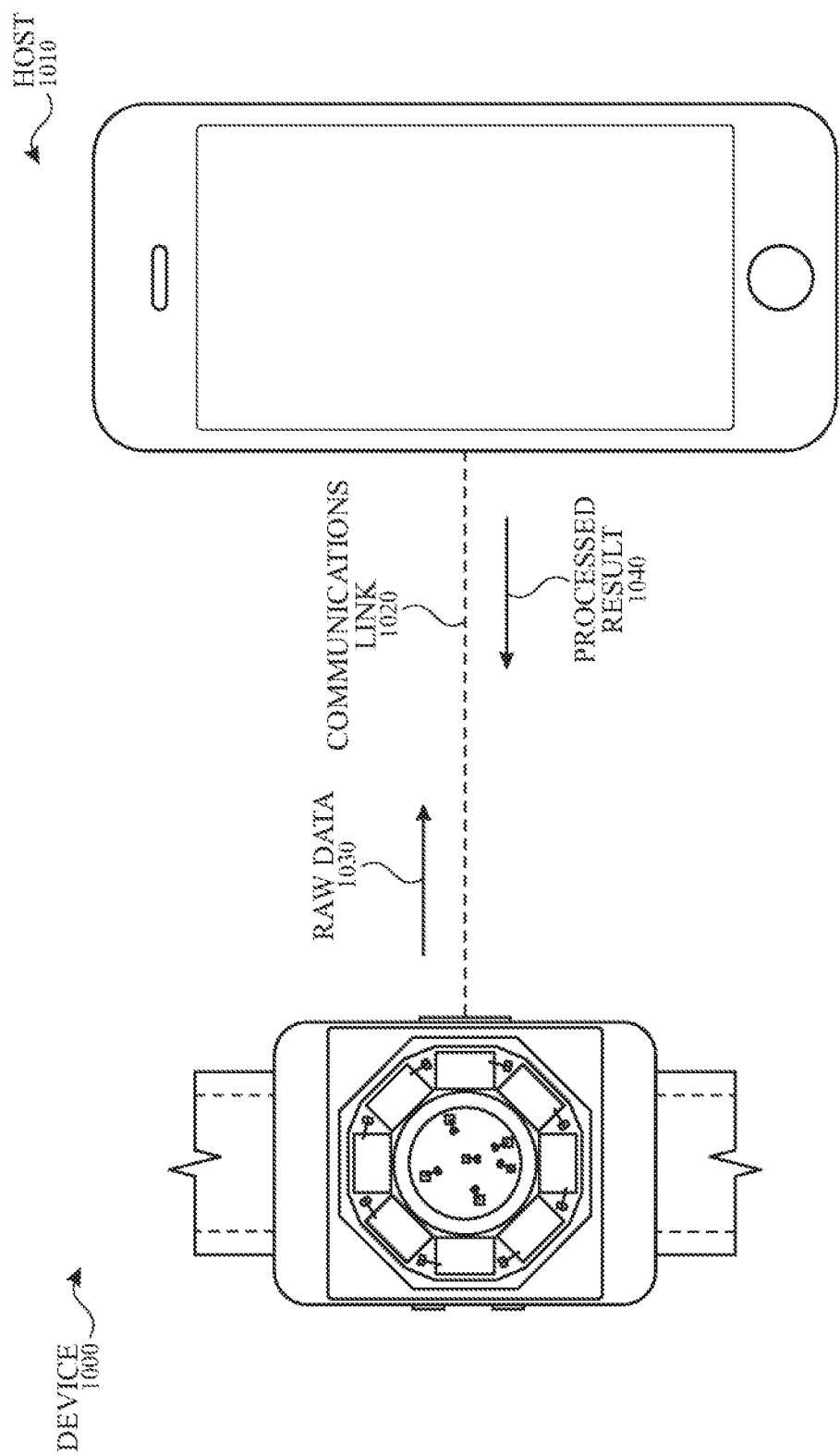
FIG. 10 illustrates an exemplary configuration in which an electronic device is connected to a host according to examples of the disclosure.

In some examples, the light detectors can measure light information and a processor can determine a PPG signal and/or perfusion index from the return light. Processing of the light information can be performed on the device as well. In some examples, processing of light information need not be performed on the device itself. FIG. 10 illustrates an exemplary configuration in which an electronic device is connected to a host according to examples of the disclosure. Host 1010 can be any device external to device 1000 including, but not limited to, any of the systems illustrated in FIGS. 1A-1C or a server. Device 1000 can be connected to host 1010 through communications link 1020. Communications link 1020 can be any connection including, but not limited to, a wireless connection and a wired connection. Exemplary wireless connections include Wi-Fi, Bluetooth, Wireless Direct and Infrared. Exemplary wired connections include Universal Serial Bus (USB), FireWire, Thunderbolt, or any connection requiring a physical cable.

In operation, instead of processing light information from the light detectors on the device 1000 itself, device 1000 can send raw data 1030 measured from the light detectors over communications link 1020 to host 1010. Host 1010 can receive raw data 1030, and host 1010 can process the light information. Processing the light information can include determining the state of the device 1000. Host 1010 can include algorithms or calibration procedures to account for differences in a user's characteristics affecting PPG signal and perfusion index. Additionally, host 1010 can include storage or memory for tracking the state of the device for diagnostic purposes. Host 1010 can send the processed result 1040 or related information back to device 1000. Based on the processed result 1040, device 1000 can notify the user or adjust its operation accordingly. By offloading the processing and/or storage of the light information, device 1000 can conserve space and power-enabling device 1000 to remain small and portable, as space that could otherwise be required for processing logic can be freed up on the device.

One aspect of the present technology is measuring, gathering, and using data available from various sources to improve methods and systems for distinguishing between a user and an object. The present disclosure contemplates that, in some instances, this gathered data may include personal information data that uniquely identifies or can be used to contact or locate a specific person. Additionally, the measured information can be delivered to the user, where additional information can be utilized to improve the delivery of measured information, analysis, or any other content that may be of interest to the users. Such personal information data can include demographic data, location-based data, telephone numbers, email addresses, twitter ID's, home addresses, data or records related to a user's health or level of fitness (e.g., vital signs measurements, medication information, exercise information), date of birth, user preferences, or any other identifying or personal information.

The present disclosure recognizes that the use of such personal information data, in the present technology, can be used to the benefit of users. For example, the personal information data can be used to deliver information that is of greater interest to the user. Accordingly, use of such personal information data can be to enable timely and controlled delivery of the measured information, analysis, or other content to the user. Further, other uses for personal information that benefit the user are also contemplated by the present disclosure. For instance, health and fitness data may be used to provide insights into a user's general wellness, or may be used as positive feedback to individuals using technology to pursue wellness goals.

In some examples, an entity may use the personal information for collecting, analyzing, disclosing, measuring, transferring, and/or storing the measured information, analysis, or other user-specific content. The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users and should be updated as the collection and/or use of data changes. Personal information from users should be collected for legitimate and reasonable uses of the entity and not shared (e.g., sold) outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. These privacy policies and/or privacy practices can be generally recognized as meeting (or exceeding) industry or governmental requirements for private and secure personal information and should be implemented and consistently used. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence, different privacy practices should be maintained for different personal data types in each country.

Despite the foregoing, the present disclosure also contemplates examples in which users control (e.g., selectively block or restrict access to) use of the personal information data. That is, the present disclosure contemplates that hardware and/or software elements can be provided to provide the user(s) with this control. For example, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the appl. The user may also select which information (e.g., email address) to withhold.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health-related applications, data de-identification can be used to protect a user's privacy. De-identification may be facilitated, when appropriate, by removing specific identifies (e.g., date of birth, etc.), controlling the amount or specificity of data stored (e.g., collecting location data at city level, rather than at an address level), controlling how data is stored (e.g., aggregating data across users), and/or other methods.

Therefore, although the present disclosure broadly covers use of personal information data to implement one or more various disclosed examples, the present disclosure also contemplates that the various examples can be implemented without the need for accessing such personal information data. That is, the various embodiments of the present technology are not rendered inoperable due to the lack of all or a portion of such personal information. For example, content can be selected and delivered to users by inferring preferences based on non-personal information data or a bare minimum amount of personal information, such as the content being requested by the device associated with a user, other non-personal information available, or publicly available information.

An optical sensing unit is disclosed. The optical sensing unit comprises: a plurality of first light emitters and a plurality of second light emitters; a plurality of light detectors that: detects at least a portion of a return of light emitted by the plurality of second light emitters, and generates one or more signals indicative of the detected return light; a plurality of optical components overlaying the plurality of second light emitters, wherein the plurality of optical components change one or more properties of the respective light emitted by the plurality of second light emitters; and a processor that: receives and processes the one or more signals, and determines one or more states of a device based on the one or more signals, the device including the optical sensing unit. Additionally or alternatively, in some examples, the plurality of second light emitters emits a first light and a second light, wherein the one or more properties include an angle of emission of the first light and an angle of emission of the second light, the angle of emission of the second light is different from the angle of emission of the first light. Additionally or alternatively, in some examples, the angle of emission of the first light corresponds to normal incidence relative to a surface of a window included in the device. Additionally or alternatively, in some examples, the angle of emission of the second light corresponds to non-normal incidence relative to a surface of a window included in the device. Additionally or alternatively, in some examples, at least one of the plurality of optical components splits at least one light beam in the emitted light into separate light beams. Additionally or alternatively, in some examples, at least one of the plurality of optical components including a Fresnel lens with a plurality of regions, at least two of the plurality of regions including different features, the plurality of regions including: a first region overlaying both the plurality of first light emitters and at least one second light emitter, and a second region overlaying another second light emitter. Additionally or alternatively, in some examples, the second region includes a plurality of zones, at least two of the plurality of zones including the different features. Additionally or alternatively, in some examples, the plurality of second light emitters emits a first light, a second light, and a third light, wherein the first light, the second light, and the third light are independent light beams. Additionally or alternatively, in some examples, at least one of the plurality of optical components comprises a plurality of optical control films, the plurality of optical control films including: a first optical control film overlaying one of the plurality of second light emitters and includes first features having a first angle of tilt, and a second optical control film overlaying another of the plurality of second light emitters and includes second features having a second angle of tilt, the second angle of tilt different from the first angle of tilt. Additionally or alternatively, in some examples, the first angle of tilt is towards an opposite direction than the second angle of tilt. Additionally or alternatively, in some examples, the plurality of optical control films includes a third optical control film optically coupled to the plurality of light detectors, the third optical control film being different from the first and second optical control films. Additionally or alternatively, in some examples, at least one second light emitter is located at a first edge of the optical sensing unit, at least another second light emitter is located at a second edge of the optical sensing unit, and further wherein the at least one second light emitter emits light towards the first edge, and the at least another second light emitter emits light towards the second edge. Additionally or alternatively, in some examples, the at least one second light emitter is located at a first edge of the optical sensing unit, at least another second light emitter is located at a second edge of the optical sensing unit, and further wherein the at least one second light emitter emits light towards the second edge, and the at least another second light emitter emits light towards the first edge. Additionally or alternatively, in some examples, the plurality of light detectors is further configured to detect a return of light emitted by the plurality of first light emitters.

A method for operating a device is disclosed. The method comprises: measuring one or more physiological parameters of a user using a plurality of first light emitters; and determining a state of the device comprising: emitting a first light using at least one second light emitter, the at least one second light emitter; detecting a return of the first light and generating a first signal indicative of the returned first light; emitting a second light using at least one another second light emitter, the at least one another second light emitter; detecting a return of the second light and generating a second signal indicative of the returned second light; determining a value using at least the first and second signals; and determining whether the value meets one or more criteria; and determining the state of the device in accordance with the determination of whether the value meets the one or more criteria. Additionally or alternatively, in some examples, the measurement of the one or more states further comprises: emitting a third light using a third light emitter; and detecting a return of the third light and generating a third signal indicative of the returned third light, wherein the value is further determined using the third signal. Additionally or alternatively, in some examples, the measurement of the one or more states further comprises: determining whether the value meets one or more second criteria; and determining a sub-state of the device in accordance with the determination of whether the value meets the one or more second criteria. Additionally or alternatively, in some examples, the method further comprises: determining whether to operate one or more processes based on the determined state of the device. Additionally or alternatively, in some examples, the one or more criteria include a confidence level meeting a threshold value, a signal-to-noise ratio meeting a threshold value, a motion state of the device matching a pre-determined motion, a position of the device matching a pre-determined position, and a battery level of the device meeting a threshold value.

A method for operating a device. The method comprises: measuring one or more physiological parameters of a user using a plurality of first light emitters; and determining a state of the device using an optical sensing unit, the determination comprising: receiving a signal from a component separate from the optical sensing unit; determining whether the signal meets one or more criteria; in accordance with the signal meeting the one or more criteria, determining the state of the device; and in accordance with the signal not meeting the one or more criteria, waiting a pre-determined amount of time before a subsequent determination.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. An optical sensing unit included in a wearable device, comprising:
a plurality of first light emitters and a plurality of second light emitters, wherein the plurality of second light emitters is positioned in a first cavity;
a plurality of light detectors that is positioned in a second cavity and that:
detects at least a portion of a return of light emitted by the plurality of second light emitters, and
generates one or more signals indicative of the detected return light;
an optical isolation positioned between the plurality of second light emitters and the plurality of light detectors within the optical sensing unit to separate the first cavity from the second cavity;
a plurality of optical components overlaying the plurality of second light emitters, wherein the plurality of optical components changes one or more properties of the respective light emitted by the plurality of second light emitters;
a window positioned over the plurality of first light emitters, the plurality of second light emitters, and the plurality of light detectors; and
a processor that:
receives and processes the one or more signals, and
determines whether the wearable device is in an on-wrist state or an off-wrist state based on the one or more signals.

2. The optical sensing unit of claim 1, wherein the plurality of second light emitters emits a first light and a second light, wherein the one or more properties include an angle of emission of the first light and an angle of emission of the second light, the angle of emission of the second light is different from the angle of emission of the first light.

3. The optical sensing unit of claim 2, wherein the angle of emission of the first light corresponds to normal incidence relative to a surface of the window.

4. The optical sensing unit of claim 2, wherein the angle of emission of the second light corresponds to non-normal incidence relative to a surface of the window.

5. The optical sensing unit of claim 1, wherein at least one of the plurality of optical components splits at least one light beam in the emitted light into separate light beams.

6. The optical sensing unit of claim 1, wherein at least one of the plurality of optical components including a Fresnel lens with a plurality of regions, at least two of the plurality of regions including different features, the plurality of regions including:
a first region overlaying both the plurality of first light emitters and at least one second light emitter, and
a second region overlaying another second light emitter.

7. The optical sensing unit of claim 6, wherein the second region includes a plurality of zones, at least two of the plurality of zones including the different features.

8. The optical sensing unit of claim 1, wherein the plurality of second light emitters emits a first light, a second light, and a third light, wherein the first light, the second light, and the third light are independent light beams.

9. The optical sensing unit of claim 1, wherein at least one of the plurality of optical components comprises a plurality of optical control films, the plurality of optical control films including:
a first optical control film overlaying one of the plurality of second light emitters and includes first features having a first angle of tilt, and
a second optical control film overlaying another of the plurality of second light emitters and includes second features having a second angle of tilt, the second angle of tilt different from the first angle of tilt.

10. The optical sensing unit of claim 9, wherein the first angle of tilt is towards an opposite direction than the second angle of tilt.

11. The optical sensing unit of claim 9, wherein the plurality of optical control films includes a third optical control film optically coupled to the plurality of light detectors, the third optical control film being different from the first and second optical control films.

12. The optical sensing unit of claim 1, wherein at least one second light emitter is located at a first edge of the optical sensing unit, at least another second light emitter is located at a second edge of the optical sensing unit, and
further wherein the at least one second light emitter emits light towards the first edge, and the at least another second light emitter emits light towards the second edge.

13. The optical sensing unit of claim 1, wherein at least one second light emitter is located at a first edge of the optical sensing unit, at least another second light emitter is located at a second edge of the optical sensing unit, and
further wherein the at least one second light emitter emits light towards the second edge, and the at least another second light emitter emits light towards the first edge.

14. The optical sensing unit of claim 1, wherein the plurality of light detectors is further configured to detect a return of light emitted by the plurality of first light emitters.

* * * * *